United States Patent
Asaad et al.

(10) Patent No.: US 10,085,773 B2
(45) Date of Patent: *Oct. 2, 2018

(54) STAGED LOCKING OF SURGICAL SCREW ASSEMBLY

(71) Applicant: SpineCraft, LLC, Westmont, IL (US)

(72) Inventors: Wagdy W Asaad, Burr Ridge, IL (US); Jayson Varghese, Niles, IL (US)

(73) Assignee: SpineCraft, LLC, Westmont, IL (US)

( * ) Notice: Subject to any disclaimer, the term of this patent is extended or adjusted under 35 U.S.C. 154(b) by 248 days.

This patent is subject to a terminal disclaimer.

(21) Appl. No.: 14/874,816

(22) Filed: Oct. 5, 2015

(65) Prior Publication Data

US 2016/0022321 A1    Jan. 28, 2016

Related U.S. Application Data

(63) Continuation of application No. 13/717,599, filed on Dec. 17, 2012, now Pat. No. 9,155,581, which is a
(Continued)

(51) Int. Cl.
*A61B 17/70* (2006.01)
*A61B 17/86* (2006.01)
(Continued)

(52) U.S. Cl.
CPC .......... *A61B 17/7032* (2013.01); *A61B 17/70* (2013.01); *A61B 17/7002* (2013.01); *A61B 17/708* (2013.01); *A61B 17/7034* (2013.01); *A61B 17/7035* (2013.01); *A61B 17/7037* (2013.01); *A61B 17/7038* (2013.01); *A61B 17/7049* (2013.01); *A61B 17/7079* (2013.01); *A61B 17/7085* (2013.01); *A61B 17/7091* (2013.01); *A61B 17/8605* (2013.01);
(Continued)

(58) Field of Classification Search
CPC ............ A61B 17/7032; A61B 17/7034; A61B 17/7035; A61B 17/7037; A61B 17/7038; A61B 17/8605; A61B 17/88
See application file for complete search history.

(56) References Cited

U.S. PATENT DOCUMENTS

| 5,207,678 A | 5/1993 | Harms et al. |
|---|---|---|
| 5,360,431 A | 11/1994 | Puno et al. |

(Continued)

OTHER PUBLICATIONS

APEX Spine System Vertebral Body Derotation Surgical Technique, Jun. 2012.

*Primary Examiner* — Larry E Waggle, Jr.
(74) *Attorney, Agent, or Firm* — Alan W. Cannon

(57) ABSTRACT

A surgical screw assembly including: a fastener including an elongate shaft having a proximal end and a distal end and a head at the proximal end. A tulip having a an internal bearing surface is provided. A distal end of the tulip has a bore therethrough defining the internal bearing surface. Locking enhancement features are configured to cooperate with the head, such that, in an unlocked configuration, the head is movable relative to the tulip; in a provisionally locked configuration, the locking enhancement features engage the head with a first polyaxial grip strength; and in a finally locked configuration, the locking enhancement features engage the head with a second polyaxial grip strength greater than the first polyaxial grip strength.

22 Claims, 26 Drawing Sheets

Related U.S. Application Data continuation-in-part of application No. 13/570,374, filed on Aug. 9, 2012, now Pat. No. 9,572,598.

(51) Int. Cl.
  *A61B 17/88* (2006.01)
  *A61B 17/68* (2006.01)
  *A61B 90/00* (2016.01)

(52) U.S. Cl.
  CPC .............. *A61B 17/88* (2013.01); *A61B 90/03* (2016.02); *A61B 2017/681* (2013.01); *A61B 2090/037* (2016.02)

(56) References Cited

U.S. PATENT DOCUMENTS

| | | |
|---|---|---|
| 5,474,555 A | 12/1995 | Puno et al. |
| 5,624,442 A | 4/1997 | Mellinger et al. |
| RE37,665 E | 4/2002 | Ralph et al. |
| 6,905,500 B2 | 6/2005 | Jeon et al. |
| 7,144,396 B2 | 12/2006 | Shluzas |
| 7,306,606 B2 | 12/2007 | Sasing |
| 7,338,491 B2 | 3/2008 | Baker et al. |
| 7,682,377 B2 | 3/2010 | Konieczynski et al. |
| 7,722,652 B2 | 5/2010 | Justis et al. |
| 7,727,261 B2 | 6/2010 | Barker et al. |
| 7,766,915 B2 | 8/2010 | Jackson |
| 7,785,354 B2 | 8/2010 | Biedermann et al. |
| 7,867,258 B2 | 1/2011 | Drewry et al. |
| 7,879,075 B2 | 2/2011 | Shluzas |
| 7,896,902 B2 | 3/2011 | Jeon et al. |
| 7,901,435 B2 | 3/2011 | Slivka et al. |
| 7,942,909 B2 | 5/2011 | Hammill, Sr. et al. |
| 7,951,173 B2 | 5/2011 | Hammill, Sr. et al. |
| 7,955,363 B2 | 6/2011 | Richelsoph |
| 7,967,849 B2 | 6/2011 | Carson et al. |
| 8,021,397 B2 | 9/2011 | Farris et al. |
| 8,057,519 B2 | 11/2011 | Justis et al. |
| 8,075,603 B2 | 12/2011 | Hammill, Sr. et al. |
| 8,080,036 B2 | 12/2011 | Shim et al. |
| 8,088,152 B2 | 1/2012 | Schumacher |
| 8,128,667 B2 | 3/2012 | Jackson |
| 8,137,387 B2 | 3/2012 | Garamszegi |
| 8,162,989 B2 | 4/2012 | Khalili |
| 8,167,910 B2 | 5/2012 | Nilsson |
| 9,155,581 B2 * | 10/2015 | Asaad ................ A61B 17/8605 |
| 2004/0102781 A1 | 5/2004 | Jeon |
| 2007/0049933 A1 | 3/2007 | Ahn et al. |
| 2008/0234757 A1 | 9/2008 | Jacofsky et al. |
| 2009/0105769 A1 | 4/2009 | Rock et al. |
| 2009/0105771 A1 | 4/2009 | Lei et al. |
| 2009/0163962 A1 * | 6/2009 | Dauster ............. A61B 17/7032 606/305 |
| 2010/0094343 A1 | 4/2010 | Pham et al. |
| 2010/0145394 A1 | 6/2010 | Harvey et al. |
| 2010/0204735 A1 | 8/2010 | Gephart et al. |
| 2010/0305621 A1 | 12/2010 | Wang et al. |
| 2011/0178558 A1 | 7/2011 | Barry |
| 2011/0196430 A1 * | 8/2011 | Walsh ................ A61B 17/7037 606/305 |
| 2014/0046374 A1 | 2/2014 | Asaad et al. |
| 2014/0046385 A1 | 2/2014 | Asaad et al. |

\* cited by examiner

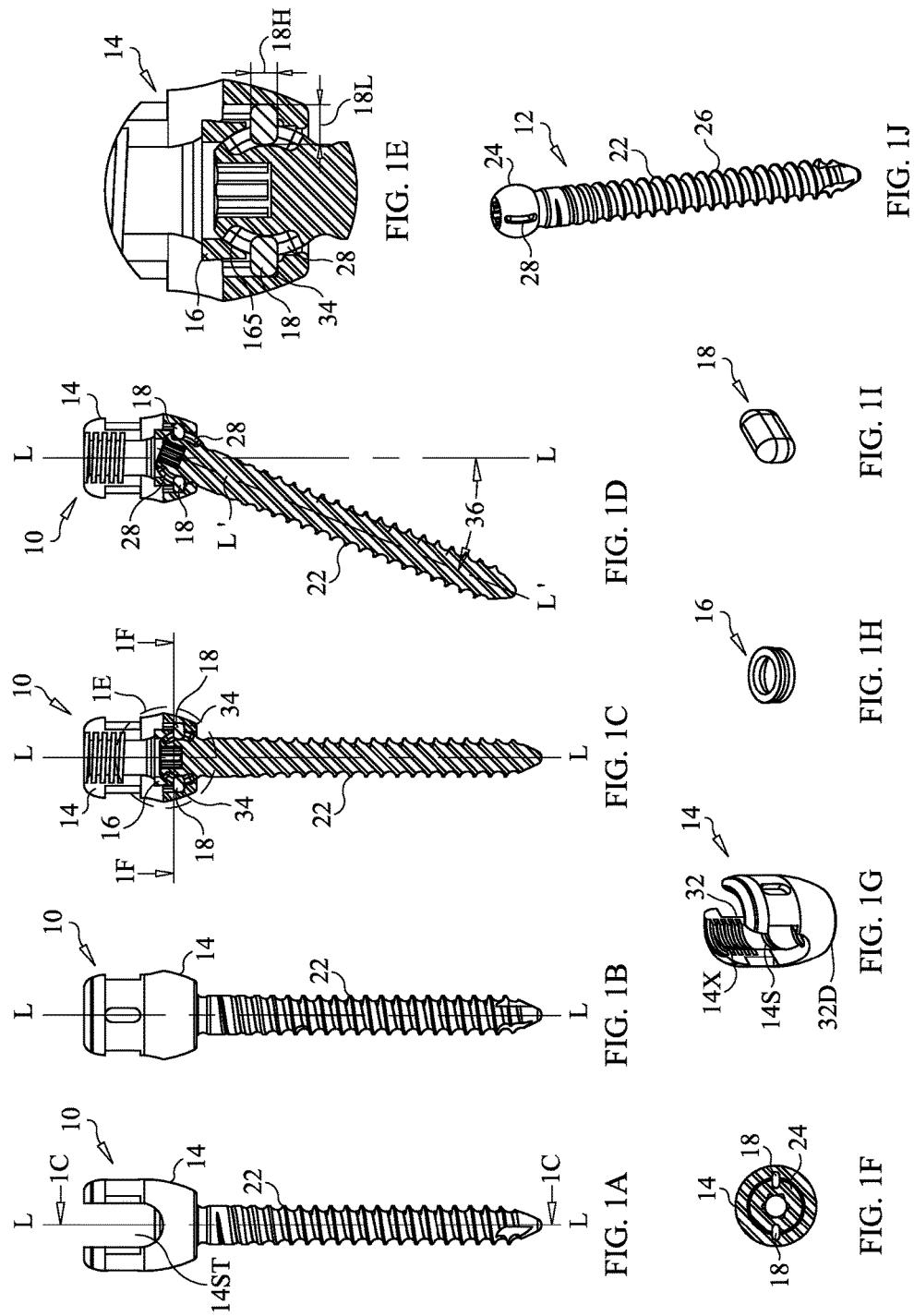

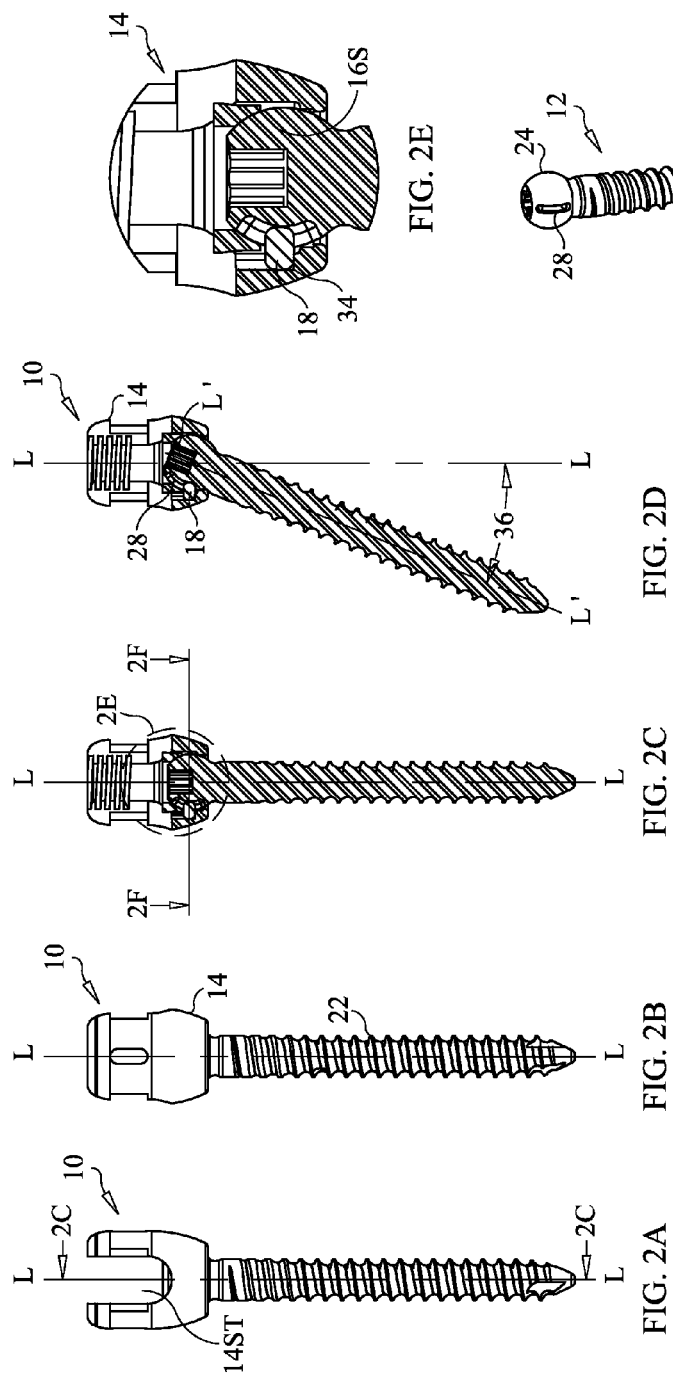

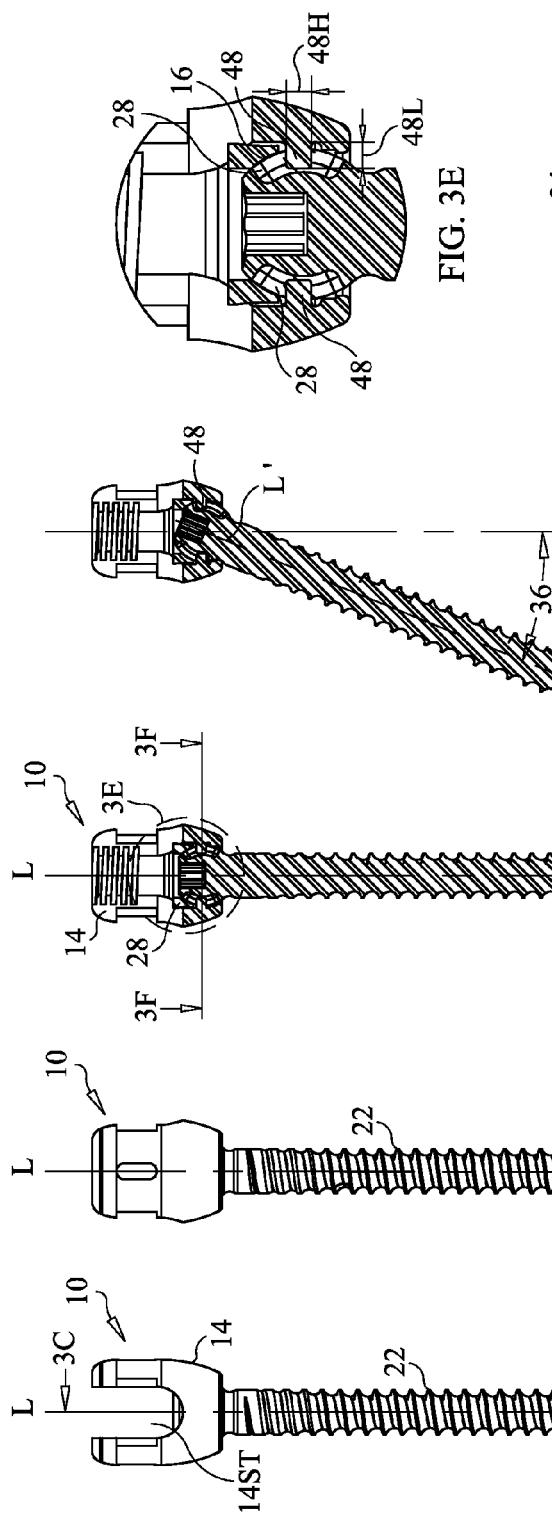

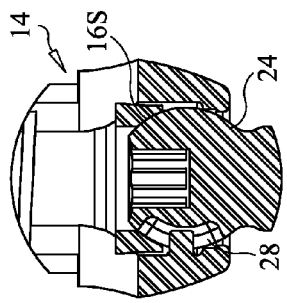
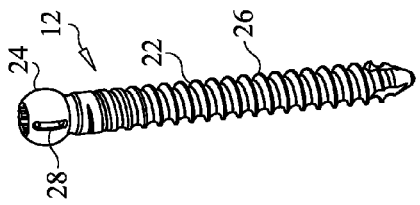
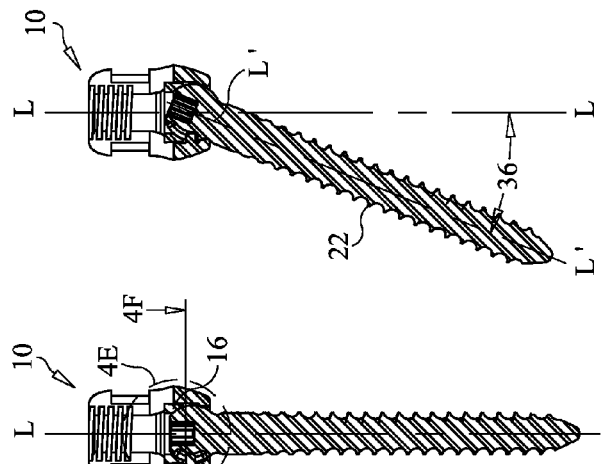
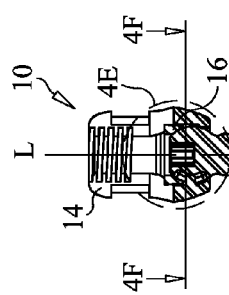
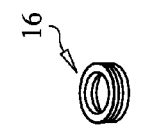
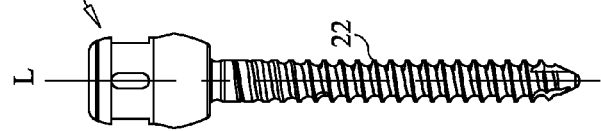
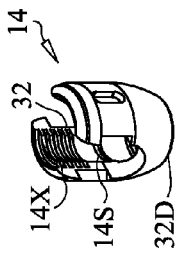
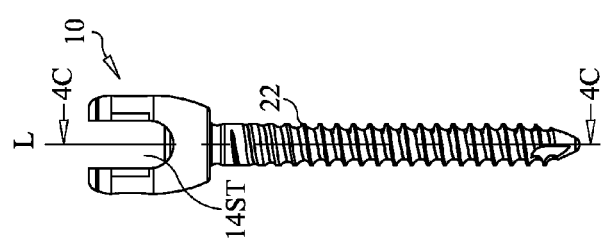
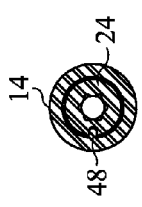

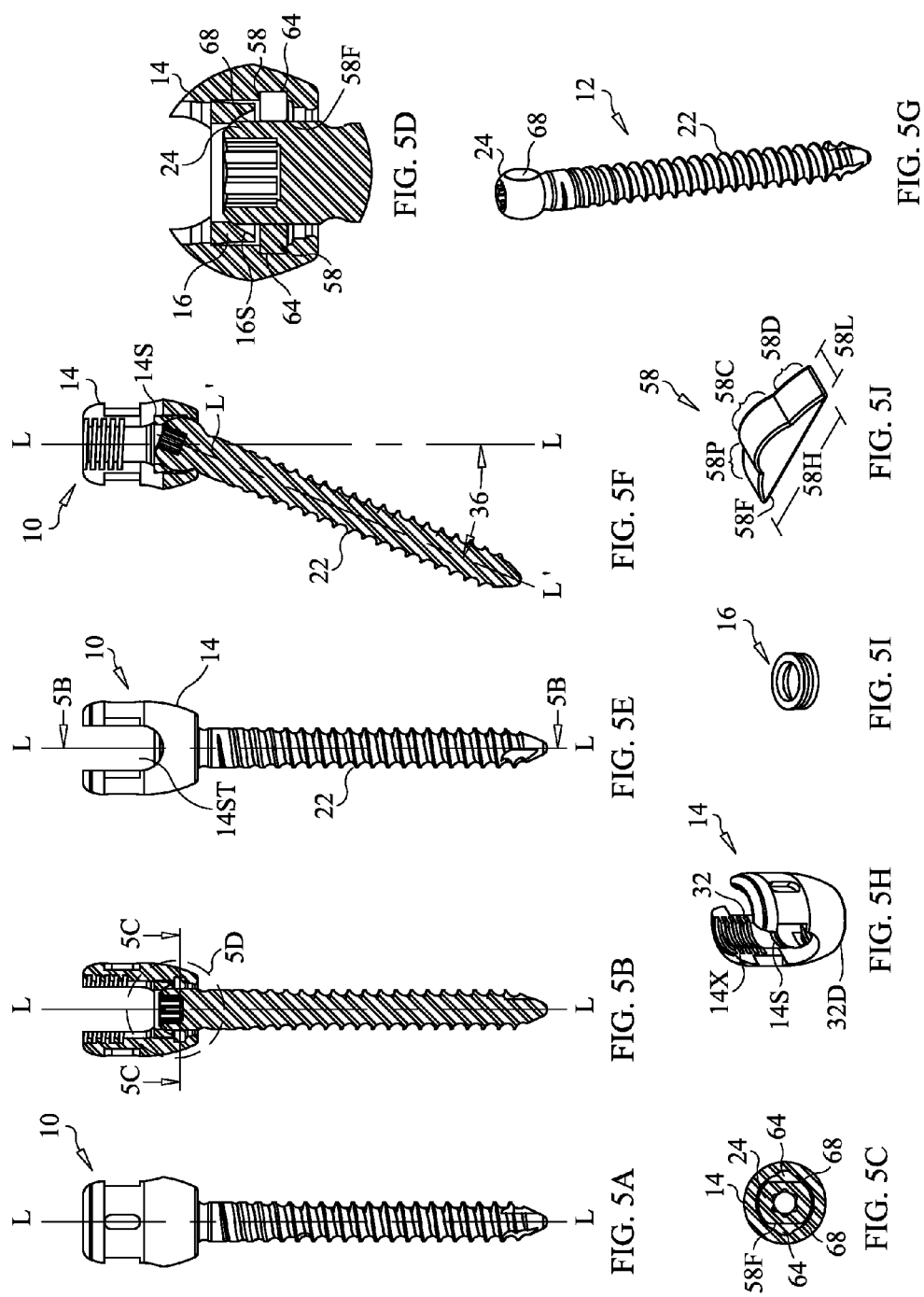

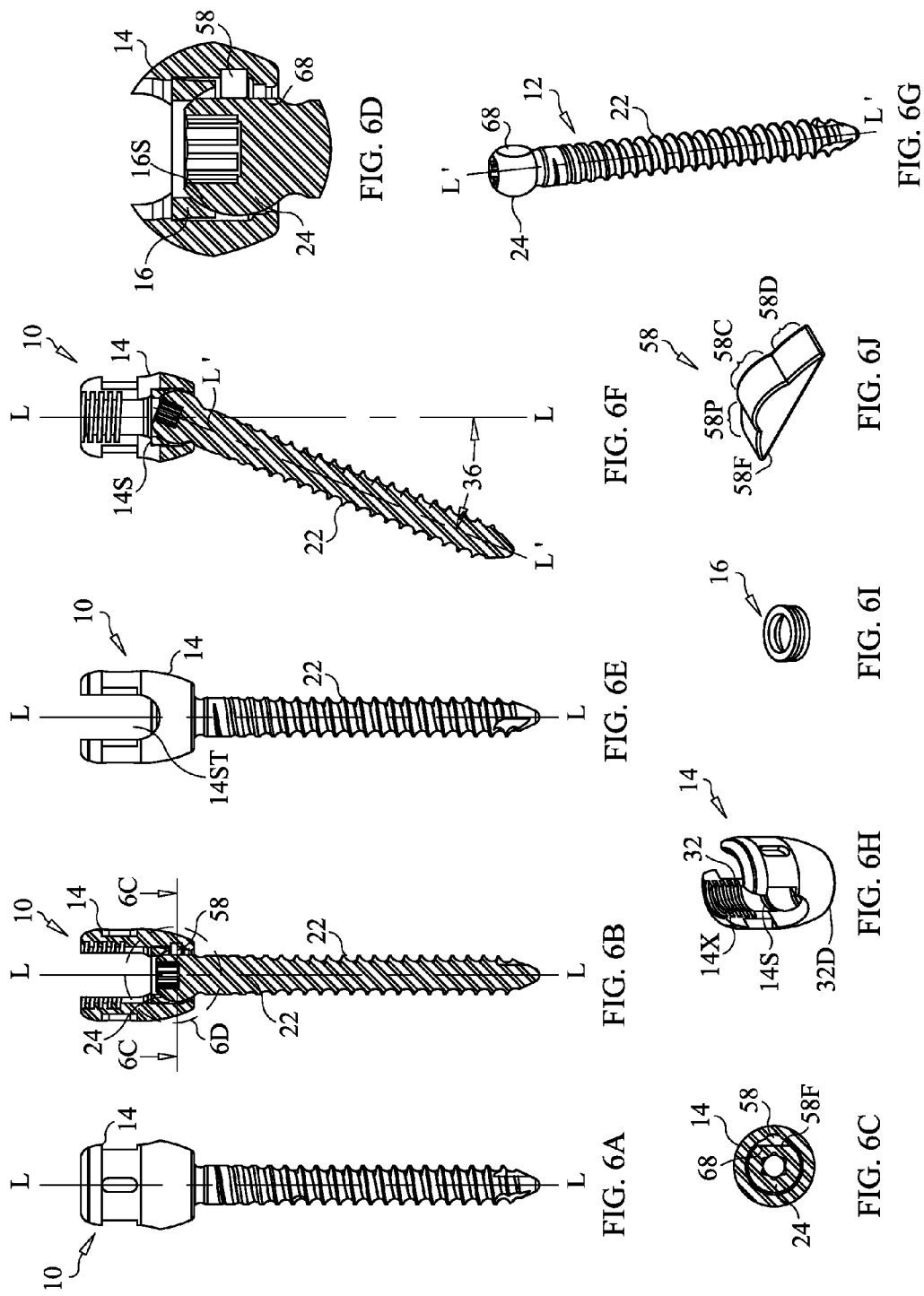

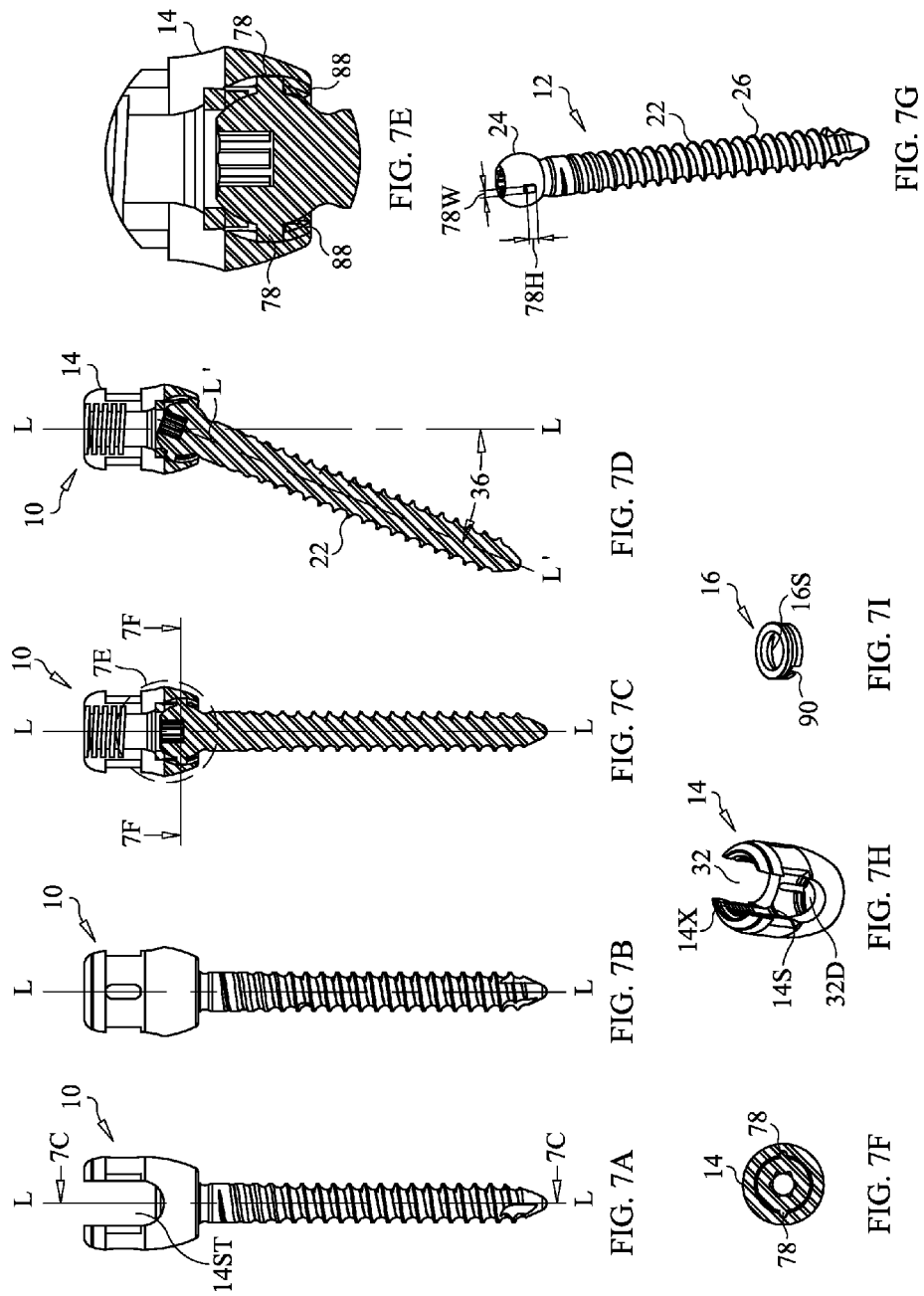

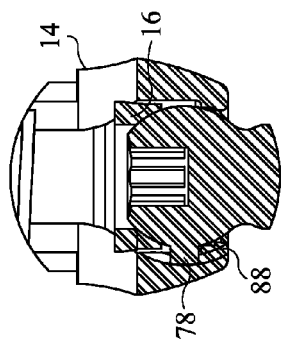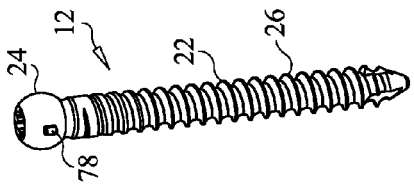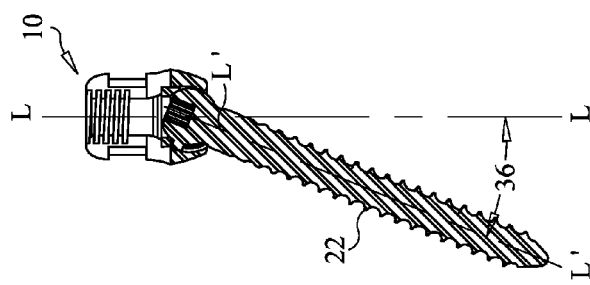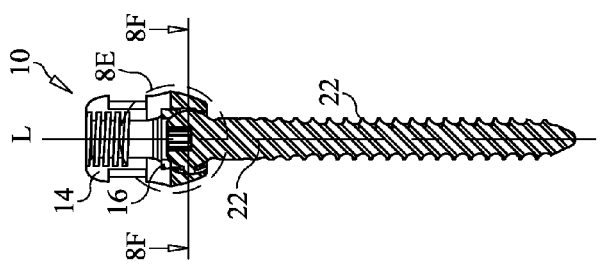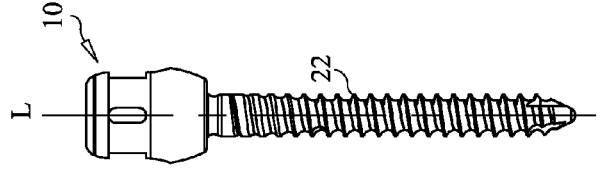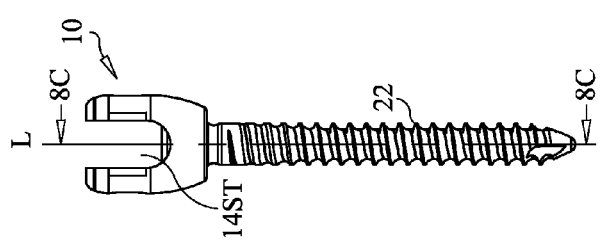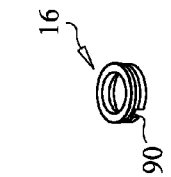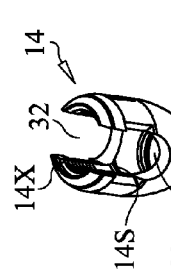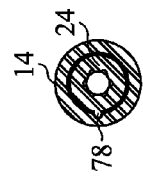

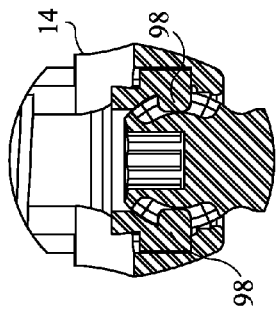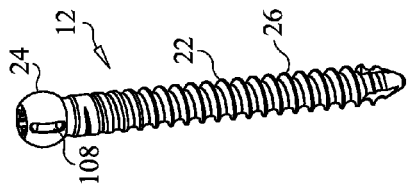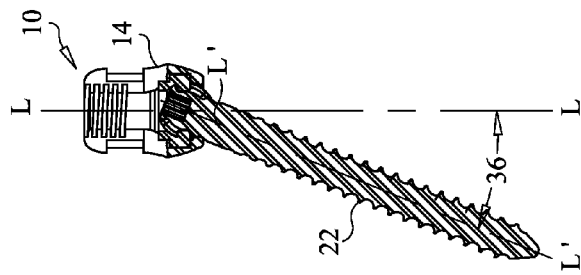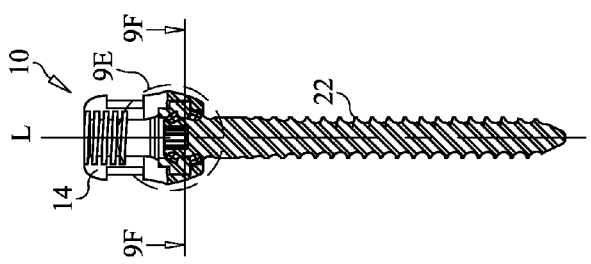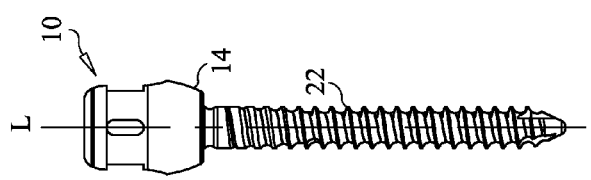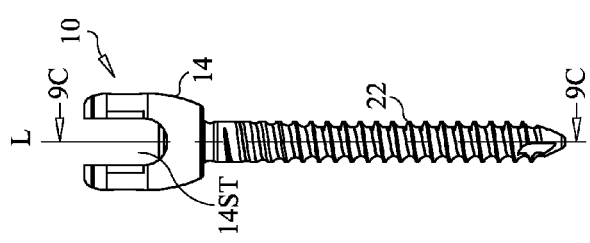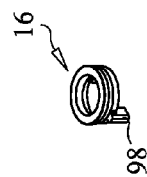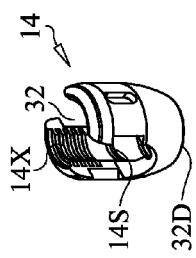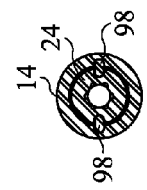

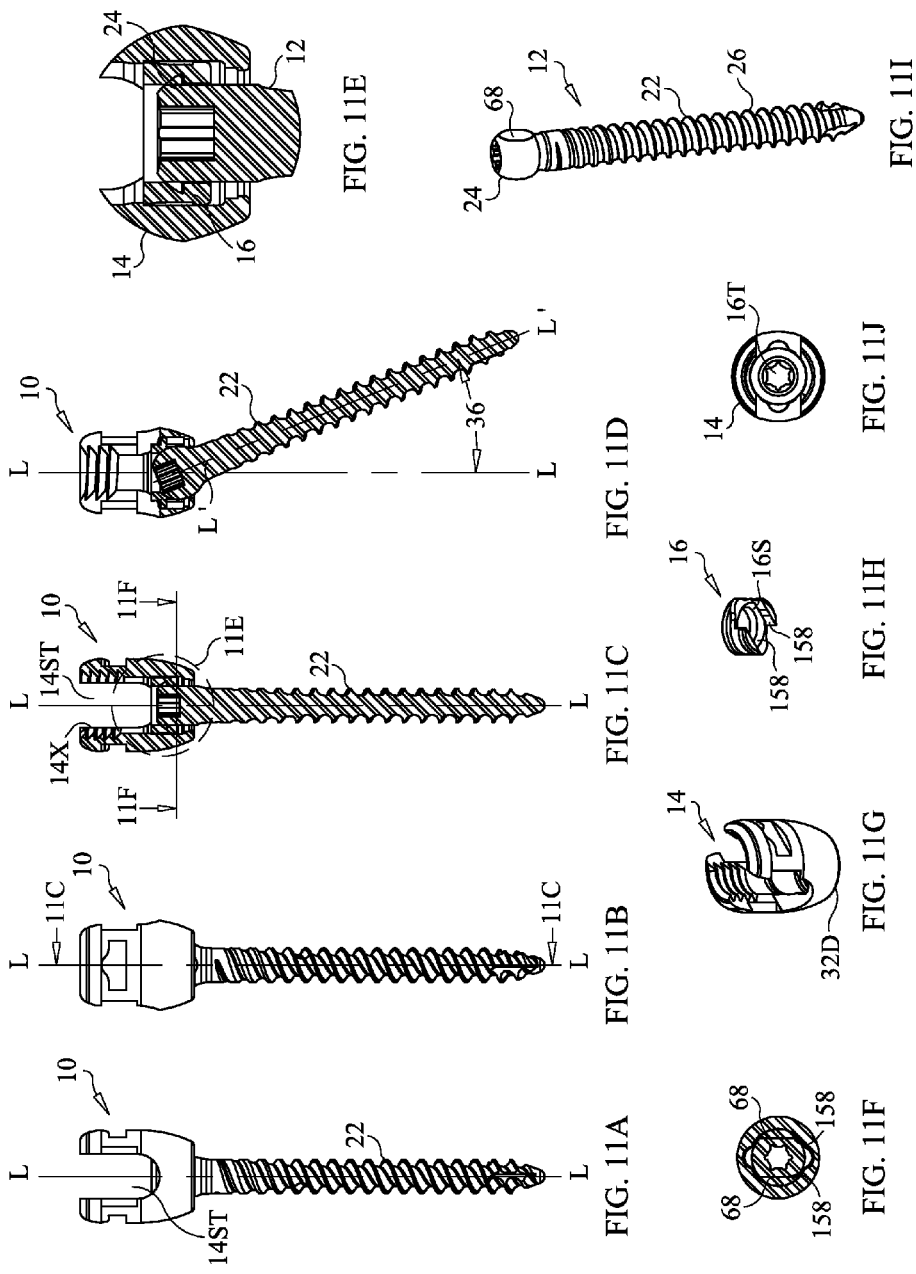

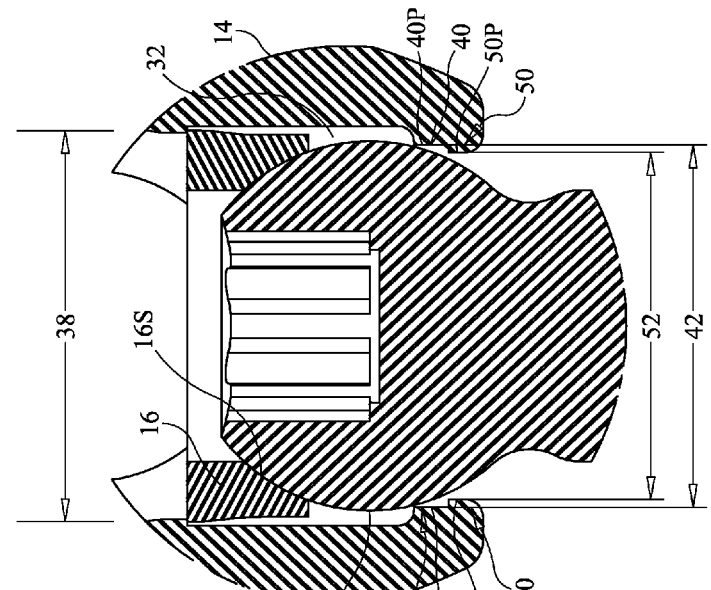
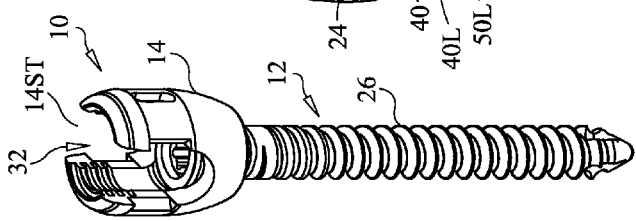
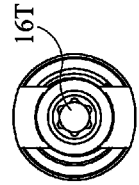
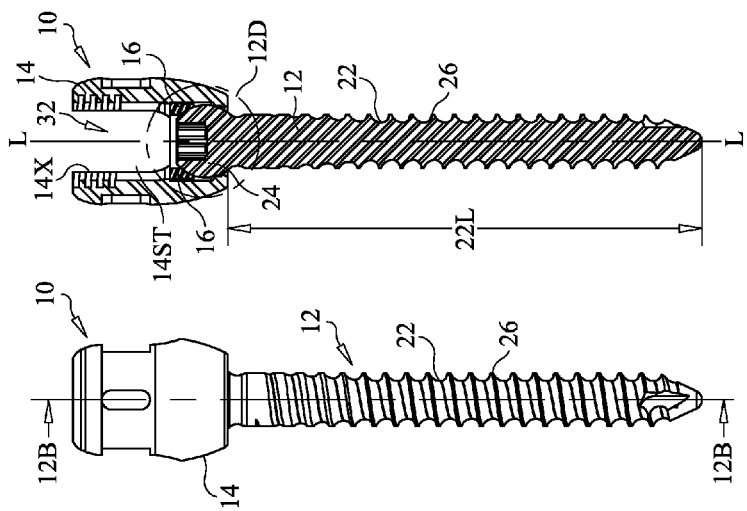
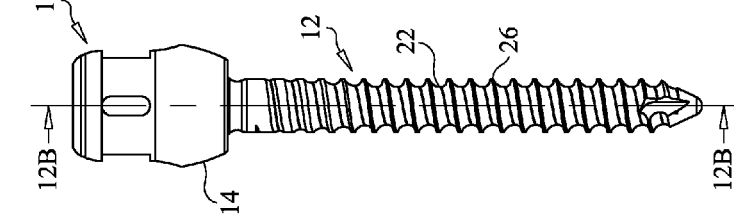

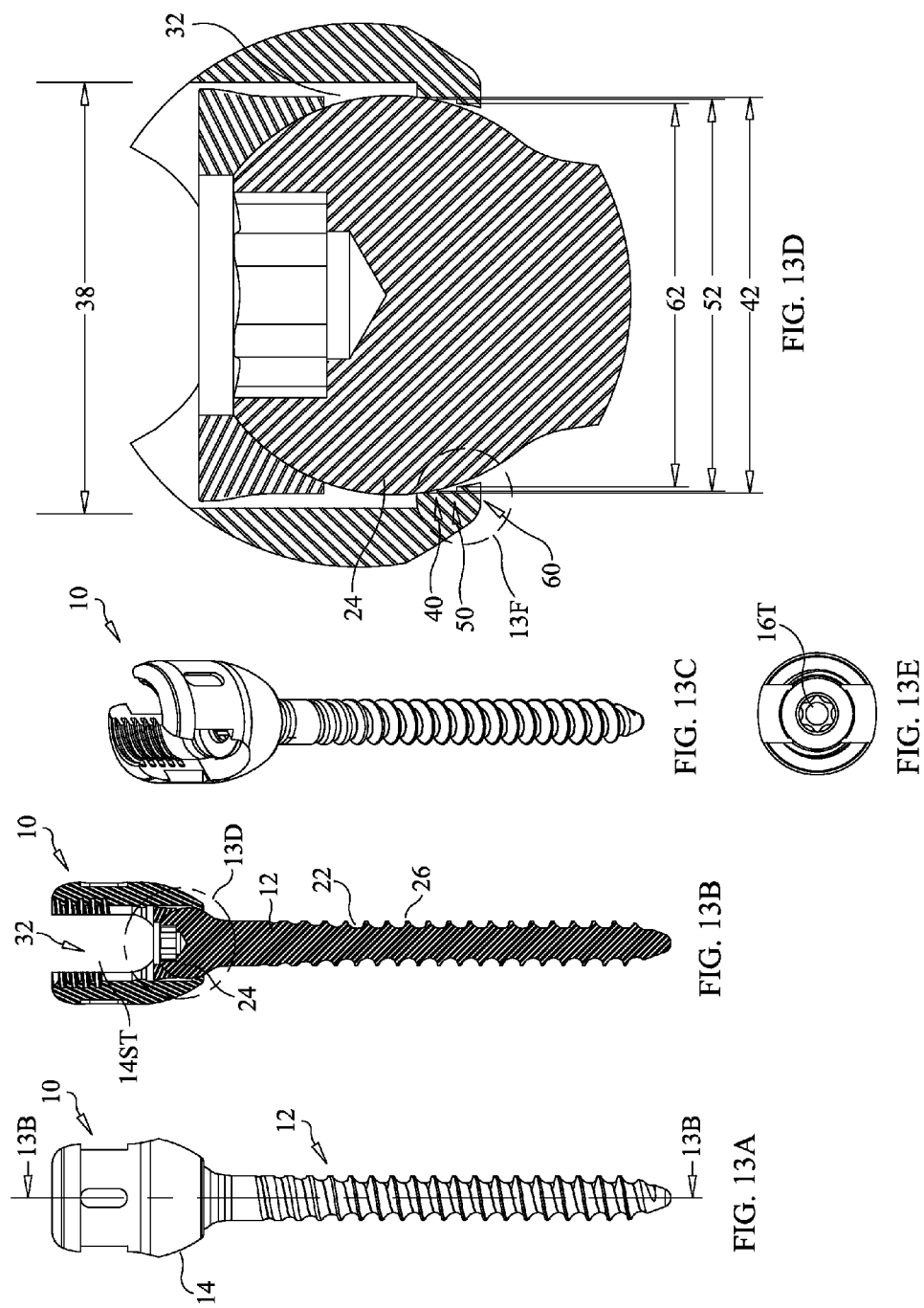

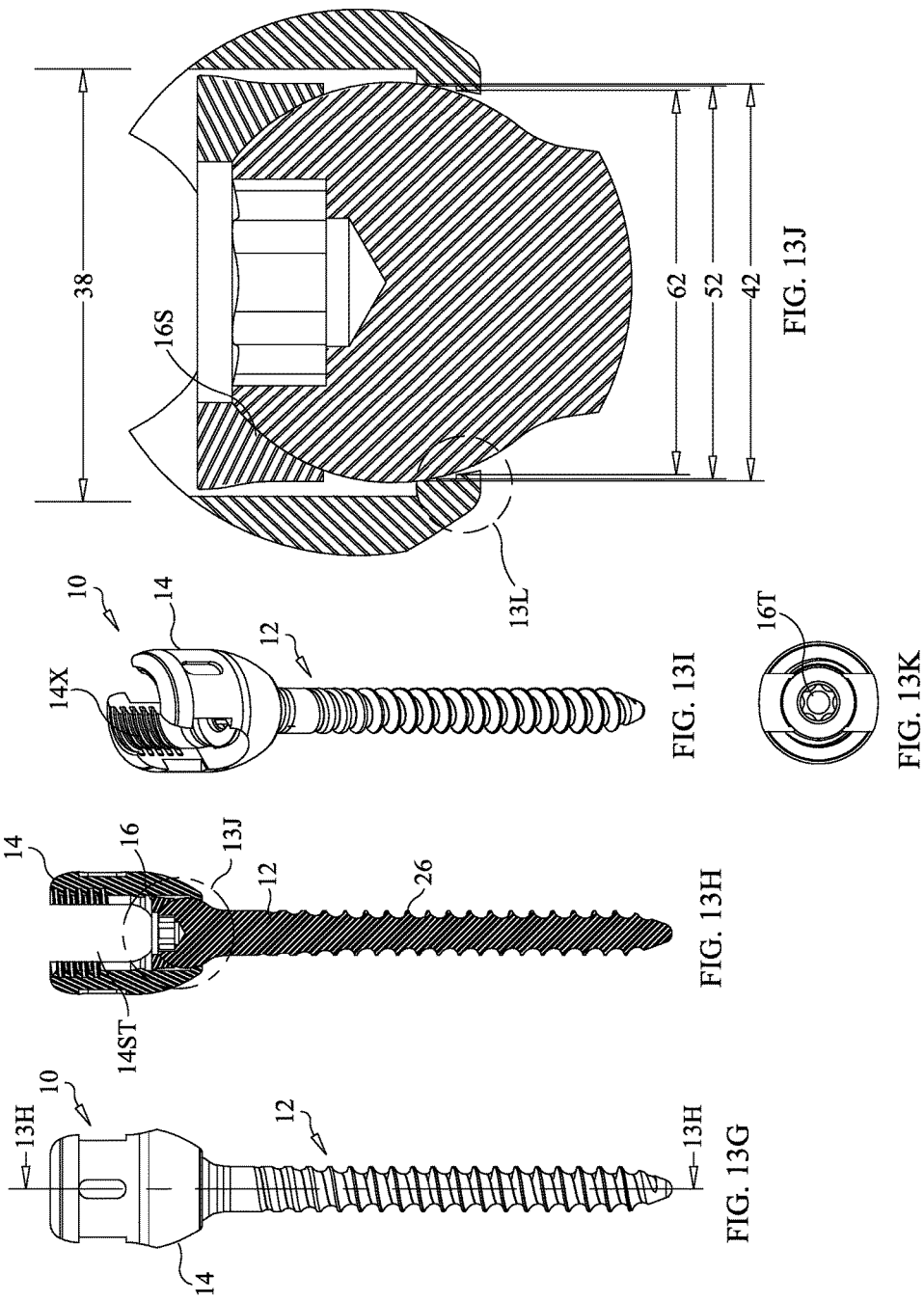

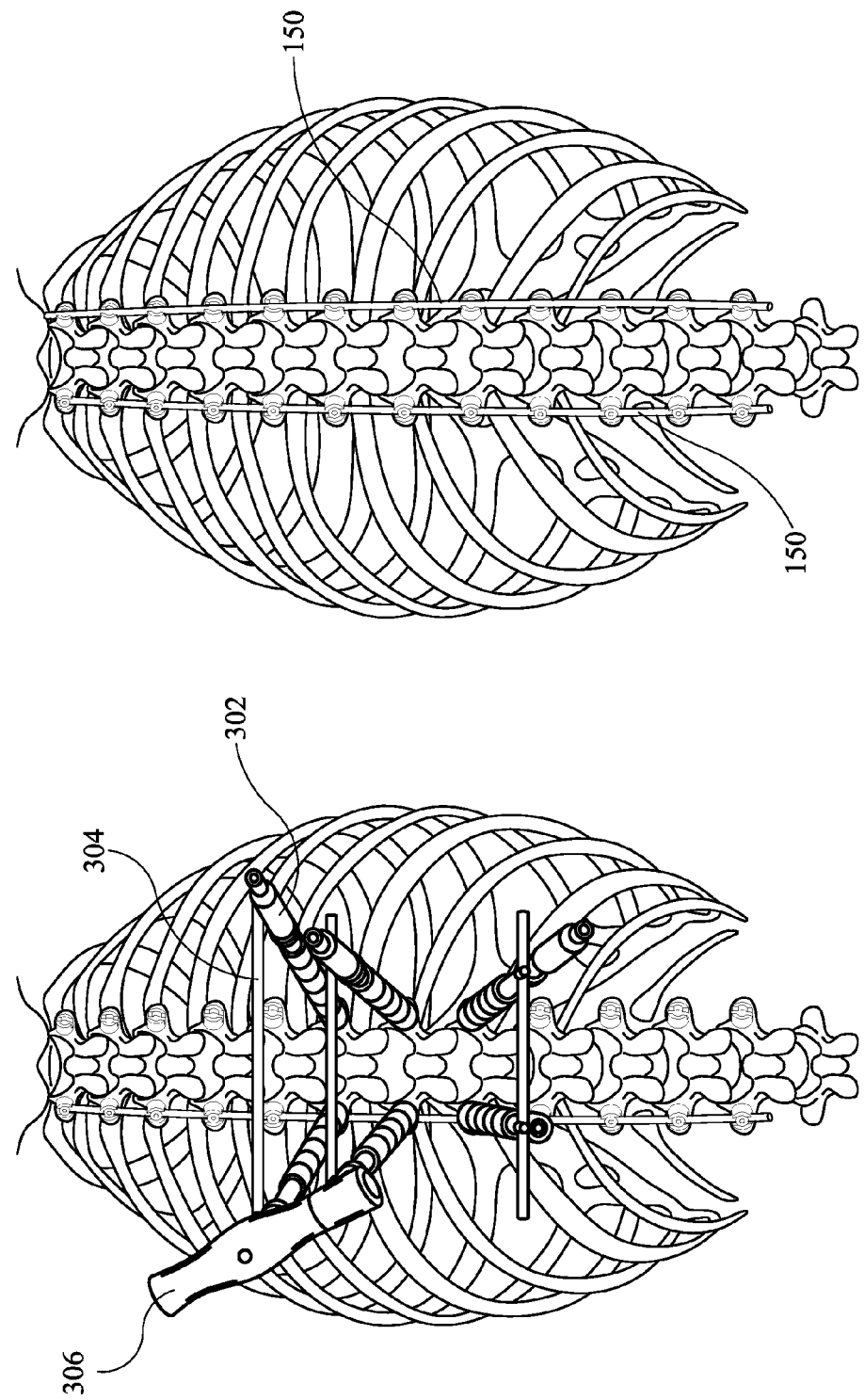

STAGED LOCKING OF SURGICAL SCREW ASSEMBLY

CROSS-REFERENCE

This application is a continuation application of co-pending application Ser. No. 13/717,599, filed Dec. 17, 2012, which is a continuation-in-part application of application Ser. No. 13/570,374, filed Aug. 9, 2012 and titled "Uniplanar Surgical Screw Assembly", both of which applications are hereby incorporated herein, in their entireties, by reference thereto, and to which applications we claim priority under 35 USC § 120. This application also references Application Ser. No. 13/717,565, filed Dec. 17, 2012, which issued as U.S. Pat. No. 9,034,022 on May 19, 2015, titled "Locking Force Augmentation Features for Polyaxial Screw Assembly", which application and patent are hereby incorporated herein, it their entireties, by reference thereto.

FIELD OF THE INVENTION

The present invention relates to the field of orthopedic surgery, in particular to devices, systems and assemblies for stabilizing and/or fixing bones and/or joints in a patient. More particularly, the present invention relates to polyaxial attachment assemblies including mechanisms for locking the same.

BACKGROUND OF THE INVENTION

The fixation and/or stabilization of bones and/or bone fragments is/are commonly required by orthopedic surgeons to treat injuries such as fractures or disease. To accomplish this, the bones/bone fragments can be joined by a rod, plate or the like, which is fixed to the bones/bone fragments via fasteners such as screws, pins or the like. The connection by the rod(s), plate(s) or the like maintains the bones/bone fragments in a desired orientation and/or at desired spacings, positions, etc. Different situations often require the adjustment of such spacings or orientations, or the removal of the apparatus, sometimes with replacement by another apparatus. For these reasons it is useful to provide fasteners that can be fixed or released, and can also articulate to adjust relative to the rod, plate, or the like, as required by the arrangement of the bones/bone fragments being treated.

In spinal surgery, it is often necessary to secure various implants to the vertebrae and interconnect the vertebrae by attaching one or more rods or plates to the implants. Due to the complex curvature of the spine, as well as irregularities of the same that often need to be treated, it is often difficult to align a rod or plate with all of the implants/fasteners fixed to the various vertebrae to be connected via the rod or plate. By providing fasteners that have some articulation ability, this allows more flexibility in joining the fasteners (and thus the vertebrae that they are attached to) to a rod or plate in the orientations needed.

In some surgeries, it is necessary to span multiple vertebrae of the spine with rods that provide stabilizing forces to the vertebrae to help maintain the desired orientations of the vertebrae o maintain a desired curvature in the spine. In these instances, uniplanar fasteners that allow pivoting in only one plane can be useful, as opposed to the more commonly used polyaxial screws, as polyaxial screws may be more likely to fail by rotating rather than withstanding a lateral force applied to the rod therethrough.

In any case, once the polyaxial or uniplanar fastener has been articulated to the desired angular position of the screw shaft relative to the tulip, there needs to be a mechanism for maintaining that angular position/orientation in a fixed manner, as the orientation should be maintained upon completing the procedure. There is a continuing need for improved fixation mechanisms to maintain fasteners in their desired orientation during use after completion of the procedure. There is a continuing need for improved fixation mechanism that enhance the fixation of fasteners in their desired orientations. It would also be advantageous to provide fasteners with provisional locking capabilities, so that an orientation can be changed, if desired, while still maintaining the ability to relock the fastener with effective locking maintenance force.

SUMMARY OF THE INVENTION

In one aspect of the present invention, a fastener is provided including an elongate shaft having a proximal end and a distal end and a head at the proximal end, the head having an external surface; a tulip having a tulip proximal end portion, a tulip distal end portion, an external surface and an internal bearing surface, said tulip distal end having a bore therethrough defining the internal bearing surface and having a diameter dimensioned to allow the distal end of the elongate shaft to pass therethrough; and locking enhancement features configured to cooperate with the head; wherein, in an unlocked configuration, the head is movable relative to the tulip and the locking enhancement features; in a provisionally locked configuration, the locking enhancement features engage the head with a first polyaxial grip strength; and in a finally locked configuration, the locking enhancement features engage the head with a second polyaxial grip strength, the second polyaxial grip strength being greater than the first polyaxial grip strength.

In at least one embodiment, the locking enhancement features comprise a set of the locking enhancement features; wherein a first subset of the locking enhancement features contact the head in the unlocked configuration; wherein the first subset and a second subset of the locking enhancement features contact the head in the provisionally locked configuration; and wherein the first subset, the second subset and a third subset of the locking enhancement features contact the head in the finally locked configuration.

In at least one embodiment, the fastener is placed in the provisionally locked configuration by applying a provisional locking compression force between the head and the tulip.

In at least one embodiment, the fastener is maintained in the provisionally locked configuration after removal of the provisional locking compression force.

In at least one embodiment, when implanted in a vertebra of a spine of a patient, when in the provisionally locked configuration, and when the provisional locking compression force has been removed, the provisionally locked configuration has sufficient locking strength to prevent relative movement between the tulip and the head when the tulip is driven to cause rotation of the vertebra.

In at least one embodiment, the fastener is placed in the finally locked configuration by applying a final locking compression force between the head and the tulip, wherein the final compression force is greater than a provisional locking compression force required to place the fastener in the provisionally locked configuration.

In at least one embodiment, the locking enhancement features are integral with the tulip.

In at least one embodiment, the locking enhancement features extend inwardly from the internal bearing surface.

In at least one embodiment, the locking enhancement features comprise: a first step feature located at a distal end portion of the bore and extending inwardly from the bore, the first step feature reducing the diameter of the bore to allow the distal end of the elongate shaft to pass therethrough, but prevent passage of the head therethrough as a portion of the first step feature contacts the head; and a second step feature located at a distal end portion of the bore, distally of the first step feature, the second step feature further reducing the diameter of the bore to a dimension less than a dimension established by the first step feature, the further reduced diameter allowing the distal end of the elongate shaft to pass therethrough, but preventing passage of the head therethrough as a portion of the second step feature contacts the head and a portion of the first step feature contacts the head.

In at least one embodiment, the locking enhancement features further comprise a third step feature located at a distal end portion of the bore, distally of the second step feature, the third step feature still further reducing the diameter of the bore to a dimension less than a dimension established by the second step feature, the still further reduced diameter allowing the distal end of the elongate shaft to pass therethrough, but preventing passage of the head therethrough as a portion of the third step feature contacts the head, a portion of the second step feature contacts the head and a portion of the first step feature contacts the head.

In at least one embodiment, the assembly further includes a driving member configured to engage a proximal end portion of the tulip and to establish a compression force between the locking enhancement features and the head.

In at least one embodiment, the tulip further comprises a slot through the proximal end portion extending transverse to the bore, the slot configured to receive a support member; wherein when the support member is received in the slot, when in the provisionally locked configuration, the tulip is prevented from movement relative to the head, but is rotatable relative to the support member; and, wherein in the finally locked configuration, the tulip is prevented from movement relative to the head and is prevented from movement relative to the support member.

In at least one embodiment, the assembly further includes reduction tabs extending proximally of the tulip and extending the slot.

In at least one embodiment, the assembly further includes a saddle, the saddle being configured and dimensioned to be fitted in the tulip proximally of and against the head.

In another aspect of the present invention, a method of operating a surgical screw assembly is provided, including: providing a surgical screw assembly comprising: a fastener including an elongate shaft having a proximal end and a distal end and a head at the proximal end, the head having an external surface; a tulip having a tulip proximal end portion, a tulip distal end portion, an external surface and an internal bearing surface, the tulip distal end having a bore therethrough defining the internal bearing surface and having a diameter dimensioned to allow the distal end of the elongate shaft to pass therethrough; and locking enhancement features configured to cooperate with the head; wherein, in an unlocked configuration, the tulip is free to rotate relative to the head; attaching a support member to the assembly; applying a first compression force between the tulip and the locking enhancement features, wherein the locking enhancement features engage with the head to place the assembly in a provisionally locked configuration; wherein, in the provisionally locked configuration, the tulip is prevented from rotating relative to the head, but the tulip is movable relative to the support member.

In at least one embodiment, the fastener further comprises reduction tabs extending proximally form the tulip, and wherein the attaching a support member comprises positioning the support member between the reduction tabs, relatively moving the fastener and the support member toward one another so that the support member is positioned within the tulip, and removing the reduction tabs from the tulip after the attaching a support member to the assembly.

In at least one embodiment, the method includes relatively rotating one of the support member and the tulip relative to the other, while the provisionally locked configuration prevents the tulip from rotating relative to the head.

In at least one embodiment, the method includes removing the first compression force, whereby the assembly is maintained in the provisionally locked configuration after the removing the first compression force.

In at least one embodiment, the method includes applying a second compression force greater than the first compression force between the tulip and the locking enhancement features, wherein the locking enhancement features engage with the head in a finally locked configuration; wherein, in the finally locked configuration, the tulip is prevented from rotating relative to the head, and the tulip is prevented from moving relative to the support member.

In another aspect of the present invention, a method of using a surgical screw assembly in a surgical procedure is provided, including: providing a surgical screw assembly comprising: a fastener including an elongate shaft having a proximal end and a distal end and a head at the proximal end, the head having an external surface; a tulip having a tulip proximal end portion, a tulip distal end portion, an external surface and an internal bearing surface, the tulip distal end having a bore therethrough defining the internal bearing surface and having a diameter dimensioned to allow the distal end of the elongate shaft to pass therethrough; and locking enhancement features configured to cooperate with the head; wherein, in an unlocked configuration, the tulip is free to rotate relative to the head; implanting the shaft into a vertebra of a patient; attaching a support member to the assembly; applying a first compression force between the tulip and the locking enhancement features, wherein the locking enhancement features engage with the head to place the assembly in a provisionally locked configuration; and applying a force to the tulip to rotate the vertebra relative to the support member, and rotating the tulip and the vertebra relative to the support member while the tulip is prevented from rotating relative to the shaft.

In at least one embodiment, when the vertebra has been rotated to a desired orientation, the method includes applying a second compression force greater than the first compression force between the tulip and the locking enhancement features, while maintaining the desired orientation, wherein the locking enhancement features engage with the head to place the assembly in a finally locked configuration, the vertebra is prevented from rotating relative to the support member and the tulip is prevented from rotating relative to the support member.

In at least one embodiment, the method includes applying a second force to the tulip to drive the vertebra toward or away from an adjacent vertebra.

These and other features of the invention will become apparent to those persons skilled in the art upon reading the details of the assemblies and methods as more fully described below.

BRIEF DESCRIPTION OF THE DRAWINGS

FIG. 1A is a plan view of a uniplanar surgical screw assembly according to an embodiment of the present invention.

FIG. 1B shows the assembly of FIG. 1A having been rotated about its longitudinal axis L-L by ninety degrees, relative to the view shown in FIG. 1A.

FIG. 1C is a longitudinal sectional view of the embodiment of FIG. 1A taken along line 1C-1C.

FIG. 1D shows the assembly of FIG. 1C, after pivoting the shaft relative to the tulip.

FIG. 1E is an enlarged detailed view of the portion of FIG. 1C within circle 1E.

FIG. 1F is a cross sectional view of the assembly taken along line 1F-1F in FIG. 1C.

FIG. 1G is an isolated, perspective view of the tulip component of FIG. 1A.

FIG. 1H is an isolated, perspective view of the saddle component of FIG. 1A.

FIG. 1I is an isolated, perspective view of an insert component of FIG. 1A.

FIG. 1J is an isolated, perspective view of the fastener component of FIG. 1A.

FIG. 2A is a plan view of a uniplanar surgical screw assembly according to another embodiment of the present invention.

FIG. 2B shows the assembly of FIG. 2A having been rotated about its longitudinal axis L-L by ninety degrees, relative to the view shown in FIG. 2A.

FIG. 2C is a longitudinal sectional view of the embodiment of FIG. 2A taken along line 2C-2C.

FIG. 2D shows the assembly of FIG. 2C, after pivoting the shaft relative to the tulip.

FIG. 2E is an enlarged detailed view of the portion of FIG. 2C within circle 2E.

FIG. 2F is a cross sectional view of the assembly taken along line 2F-2F in FIG. 2C.

FIG. 2G is an isolated, perspective view of the fastener of FIG. 2A.

FIG. 2H is an isolated, perspective view of the tulip component of FIG. 2A.

FIG. 2I is an isolated, perspective view of the saddle component of FIG. 2A.

FIG. 2J is an isolated, perspective view of the insert component of FIG. 2A.

FIG. 3A is a plan view of a uniplanar surgical screw assembly according to another embodiment of the present invention.

FIG. 3B shows the assembly of FIG. 3A having been rotated about its longitudinal axis L-L by ninety degrees, relative to the view shown in FIG. 3A.

FIG. 3C is a longitudinal sectional view of the embodiment of FIG. 3A taken along line 3C-3C.

FIG. 3D shows the assembly of FIG. 3C, after pivoting the shaft relative to the tulip.

FIG. 3E is an enlarged detailed view of the portion of FIG. 3C within circle 3E.

FIG. 3F is a cross sectional view of the assembly taken along line 3F-3F in FIG. 3C.

FIG. 3G is an isolated, perspective view of the fastener of FIG. 3A.

FIG. 3H is an isolated, perspective view of the tulip component of FIG. 3A.

FIG. 3I is an isolated, perspective view of the saddle component of FIG. 3A.

FIG. 4A is a plan view of a uniplanar surgical screw assembly according to another embodiment of the present invention.

FIG. 4B shows the assembly of FIG. 4A having been rotated about its longitudinal axis L-L by ninety degrees, relative to the view shown in FIG. 4A.

FIG. 4C is a longitudinal sectional view of the embodiment of FIG. 4A taken along line 4C-4C.

FIG. 4D shows the assembly of FIG. 4C, after pivoting the shaft relative to the tulip.

FIG. 4E is an enlarged detailed view of the portion of FIG. 4C within circle 4E.

FIG. 4F is a cross sectional view of the assembly taken along line 4F-4F in FIG. 4C.

FIG. 4G is an isolated, perspective view of the fastener of FIG. 4A.

FIG. 4H is an isolated, perspective view of the tulip component of FIG. 4A.

FIG. 4I is an isolated, perspective view of the saddle component of FIG. 4A.

FIG. 5A is a plan view of a uniplanar surgical screw assembly according to another embodiment of the present invention.

FIG. 5B is a longitudinal sectional view of the embodiment of FIG. 5E taken along line 5B-5B.

FIG. 5C is a cross sectional view of the assembly taken along line 5C-5C in FIG. 5B.

FIG. 5D is an enlarged detailed view of the portion of FIG. 5B within circle 5D.

FIG. 5E shows the assembly of FIG. 5A having been rotated about its longitudinal axis L-L by ninety degrees, relative to the view shown in FIG. 5A.

FIG. 5F shows the assembly of FIG. 5B, after pivoting the shaft relative to the tulip.

FIG. 5G is an isolated, perspective view of the fastener of FIG. 5A.

FIG. 5H is an isolated, perspective view of the tulip component of FIG. 5A.

FIG. 5I is an isolated, perspective view of the saddle component of FIG. 5A.

FIG. 5J is an isolated, perspective view of a flat insert component of FIG. 5A.

FIG. 6A is a plan view of a uniplanar surgical screw assembly according to another embodiment of the present invention.

FIG. 6B is a longitudinal sectional view of the embodiment of FIG. 6E taken along line 6B-6B.

FIG. 6C is a cross sectional view of the assembly taken along line 6C-6C in FIG. 6B.

FIG. 6D is an enlarged detailed view of the portion of FIG. 6B within circle 6D.

FIG. 6E shows the assembly of FIG. 6A having been rotated about its longitudinal axis L-L by ninety degrees, relative to the view shown in FIG. 6A.

FIG. 6F shows the assembly of FIG. 6B, after pivoting the shaft relative to the tulip.

FIG. 6G is an isolated, perspective view of the fastener of FIG. 6A.

FIG. 6H is an isolated, perspective view of the tulip component of FIG. 6A.

FIG. 6I is an isolated, perspective view of the saddle component of FIG. 6A.

FIG. 6J is an isolated, perspective view of the flat insert component of FIG. 6A.

FIG. 7A is a plan view of a uniplanar surgical screw assembly according to another embodiment of the present invention.

FIG. 7B shows the assembly of FIG. 7A having been rotated about its longitudinal axis L-L by ninety degrees, relative to the view shown in FIG. 7A.

FIG. 7C is a longitudinal sectional view of the embodiment of FIG. 7A taken along line 7C-7C.

FIG. 7D shows the assembly of FIG. 7C, after pivoting the shaft relative to the tulip.

FIG. 7E is an enlarged detailed view of the portion of FIG. 7C within circle 7E.

FIG. 7F is a cross sectional view of the assembly taken along line 7F-7F in FIG. 7C.

FIG. 7G is an isolated, perspective view of the fastener of FIG. 7A.

FIG. 7H is an isolated, perspective view of the tulip component of FIG. 7A.

FIG. 7I is an isolated, perspective view of the saddle component of FIG. 7A.

FIG. 8A is a plan view of a uniplanar surgical screw assembly according to another embodiment of the present invention.

FIG. 8B shows the assembly of FIG. 8A having been rotated about its longitudinal axis L-L by ninety degrees, relative to the view shown in FIG. 8A.

FIG. 8C is a longitudinal sectional view of the embodiment of FIG. 8A taken along line 8C-8C.

FIG. 8D shows the assembly of FIG. 8C, after pivoting the shaft relative to the tulip.

FIG. 8E is an enlarged detailed view of the portion of FIG. 8C within circle 8E.

FIG. 8F is a cross sectional view of the assembly taken along line 8F-8F in FIG. 8C.

FIG. 8G is an isolated, perspective view of the fastener of FIG. 8A.

FIG. 8H is an isolated, perspective view of the tulip component of FIG. 8A.

FIG. 8I is an isolated, perspective view of the saddle component of FIG. 8A.

FIG. 9A is a plan view of a uniplanar surgical screw assembly according to another embodiment of the present invention.

FIG. 9B shows the assembly of FIG. 9A having been rotated about its longitudinal axis L-L by ninety degrees, relative to the view shown in FIG. 9A.

FIG. 9C is a longitudinal sectional view of the embodiment of FIG. 9A taken along line 9C-9C.

FIG. 9D shows the assembly of FIG. 9C, after pivoting the shaft relative to the tulip.

FIG. 9E is an enlarged detailed view of the portion of FIG. 9C within circle 9E.

FIG. 9F is a cross sectional view of the assembly taken along line 9F-9F in FIG. 9C.

FIG. 9G is an isolated, perspective view of the fastener of FIG. 9A.

FIG. 9H is an isolated, perspective view of the tulip component of FIG. 9A.

FIG. 9I is an isolated, perspective view of the saddle component of FIG. 9A.

FIG. 11A is a plan view of a uniplanar surgical screw assembly according to another embodiment of the present invention.

FIG. 11B is a view of the embodiment of FIG. 11A after rotation about the longitudinal axis by ninety degrees.

FIG. 11C is a longitudinal sectional view of the embodiment of FIG. 11B taken along line 11C-11C.

FIG. 11D is a view showing the fastener angled relative to the tulip, according to an embodiment of the present invention.

FIG. 11E is an enlarged detailed view of the portion of FIG. 11C within circle 11E.

FIG. 11F is a cross-sectional view of the assembly taken along line 11F-11F in FIG. 11C FIG. 11G is an isolated, perspective view of the tulip component of FIGS. 11A-11F.

FIG. 11H is an isolated, perspective view of the saddle component of FIGS. 11A-11F.

FIG. 11I is an isolated, perspective view of the fastener component of FIGS. 11A-11F.

FIG. 11J is a proximal end view of FIG. 11B.

FIG. 12A is a plan view of a surgical screw assembly according to another embodiment of the present invention.

FIG. 12B is a longitudinal sectional view of the assembly of FIG. 12A taken along line 12B-12B.

FIG. 12C is a perspective view of the assembly shown in FIG. 12A.

FIG. 12D is an enlarged detailed view of the portion of FIG. 12B within circle 12D.

FIG. 12E is a proximal end view of the assembly of FIG. 12A.

FIG. 13Q is a proximal end view of the assembly of FIG. 13M.

FIG. 13R is an enlarged detailed view of the portion of FIG. 13P within ellipse 13R.

FIGS. 14A-14N illustrate steps that may be performed in carrying out a surgical procedure according to an embodiment of the present invention.

FIGS. 15A-15E illustrate a fastener 10 with extended reduction tabs 14T according to an embodiment of the present invention.

DETAILED DESCRIPTION OF THE INVENTION

Figure 10:
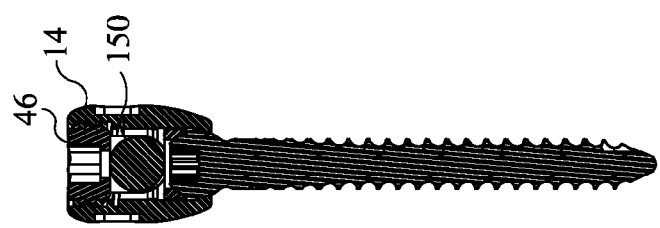
FIG. 10 is a longitudinal sectional view of an assembly locked to a rod according to an embodiment of the present invention.

Before the present assemblies, components and systems are described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise. Thus, for example, reference to "a location" includes a plurality of such locations and reference to "the screw" includes reference to one or more screws and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

The embodiments described below are directed to uniplanar and polyaxial screw assemblies for use with an orthopedic rod. Although the following description is related to such use with an orthopedic rod, for example for surgical procedures treating the spine, it is noted that the present invention as described can be used in other applicable surgical procedures, such as in other orthopedic procedures for fixing and/or aligning bones, joints, etc. Furthermore, although the specific embodiments shown in the figures and described below employ a screw as a fastener, it should be understood that other types of fasteners or securing elements may alternatively or additionally be used, including, but not limited to lamina hooks, sacral blocks, etc. Furthermore, the assemblies described can be used with a plate, shaft, channel, or the like, alternatively or in addition to use with a rod.

Definitions

The term "provisional locking" refers to a locking configuration of a fastener according to the present invention that provide sufficient polyaxial grip of a tulip relative to the head of the fastener to withstand forces applied to the tulip during a vertebral body derotation procedure, without allowing movement of the tulip relative to the head.

The term "final locking" refers to a locking configuration that a fastener is placed in to be maintained during the life of the implant. The force applied to place the fastener into the final locking configuration is greater than the force required to place the fastener into the provisional locking configuration, with all other variables kept the same.

DESCRIPTION

Referring now to FIG. 1A, a plan view of a uniplanar surgical screw assembly 10 is shown, according to an embodiment of the present invention. FIG. 1B shows assembly 10 having been rotated about its longitudinal axis L-L by ninety degrees, relative to the view shown in FIG. 1A. The assembly 10 of the embodiment of FIGS. 1A-1J includes a fastener 12 (see the isolated view of FIG. 1J), a saddle-shaped tulip 14 (see the isolated view of FIG. 1G), a saddle 16 (see the isolated view of FIG. 1H) and a pair of inserts 18 (see isolated view of an insert 18 in FIG. 1I).

Fastener 12 includes an elongate shaft 22 having a proximal end and a distal end and a head 24 at the proximal end thereof. As shown, elongate shaft 22 is a screw shaft having threads 26 therealong. Head 24 includes a pair of slots 28 that extend in a proximal-distal direction aligned with the longitudinal axis L-L.

The tulip 14 has a bore 32 therethrough that is dimensioned to allow the distal end of elongate shaft 12 to pass therethrough, but the dimension of the distal opening 32D is smaller than the largest cross-sectional dimension of the head 24, and thereby prevents passage of the head 24 therethrough, as illustrated in FIGS. 1A-1E. Inserts 18 are fixed at 34 to tulip 14 as shown in FIG. 1C, so as to protrude into the bore 32. Slots 28 are configured and dimensioned to receive the protruding ends of inserts 18, to allow inserts 18 to freely slide therein in the proximal distal direction, but to prevent movements in any other directions. Inserts 18 may be fixed to tulip 14 by adhesives, welding, press fitting and/or other fixation expedients, preferably by press fitting into receptacles 34 formed in tulip 14. As shown in FIGS. 1C-1E, slots 28 are formed diametrically opposite one another, separated by 180 degrees around the head 24. This is necessary to allow both inserts 18 to slide in the same plane, resulting in an assembly that allows the elongate shaft 22 to pivot relative to the tulip 14 in one plane only. FIG. 1C shows a longitudinal sectional view of assembly 10 taken along line 1C-1C of FIG. 1A. FIGS. 1A-1C illustrate the assembly 10 where the fastener 12 is aligned with the longitudinal axis L-L of the assembly 10 and tulip 14. FIG.

1D shows the longitudinal sectional view of FIG. 1C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14. The uniplanar range of motion may include angulation of up to about ±40°, typically a range of up to about ±22°, wherein the plus and minus values indicate the angle 36 in the direction shown in FIG. 1D and the same amount of angulation in the opposite direction in that plane.

Saddle 16 is configured and dimensioned to be fixed relative to tulip 14 while abutting the proximal portion of head 24 as shown in FIG. 1C. Saddle 16 has a concave distal surface 16s configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 1D. FIG. 1D illustrates a maximum angle 36 of pivoting, as inserts 18 make contact with the ends of slots 28, respectively. As shown in FIG. 1E, inserts 18 are centered in slots 28 when shaft 22 is aligned with the longitudinal axis L-L of the tulip 14. Alternatively, slots 28 could be asymmetrically formed so as to allow angulation 36 on one side of the longitudinal axis L-L to be greater than angulation on the other side (angulation the opposite direction).

In the embodiment shown, saddle 16 is a standard saddle and is configured and dimensioned to be retained by shoulder 14S when fitted into tulip 14, see FIG. 1G. The saddle-shaped tulip 14 further includes a slot 14ST passing therethrough, as shown in FIGS. 1A and 1G that is configured and dimensioned to receive an orthopedic rod or plate therein, in manners known in the art. Threading 14X allows a set screw 46 or the like to be torqued against the rod, plate, channel or shaft 150 to fix it relative to the tulip 14 (see FIG. 10). The saddle 16 is configured to apply compression to the head 24 to lock an orientation of the fastener 12 relative to the tulip 14, thereby even preventing the movement in the one plane that is otherwise allowed, and thus preventing movement in all planes. The set screw 46 presses on the rod, plate, channel or shaft 150 and the head 24 of the shaft is squeezed in between the saddle and the bottom of the tulip 14.

All components 12,14,16 and 18 of assembly 10 are preferably made of titanium. Alternatively, one or more components may be made of stainless steel, or other known, rigid materials used as substitute materials in the art, which may include other biocompatible metals, plastics and/or composites. The uniplanar angulation of assembly 10 may vary, but preferably has a range of about eighty degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The height 18H of insert 18 is about 1 mm to about 2 mm, typically about 1.5 mm. The length 18L: of insert 18 is about 1.5 mm to about 3 mm, typically about 2.25 mm.

Referring now to FIG. 2A, a plan view of a uniplanar surgical screw assembly 10 is shown, according to another embodiment of the present invention. FIG. 2B shows assembly 10 having been rotated about its longitudinal axis L-L by ninety degrees, relative to the view shown in FIG. 2A. The assembly 10 of the embodiment of FIGS. 2A-2J includes a fastener 12 (see the isolated view of FIG. 2G), a saddle-shaped tulip 14 (see the isolated view of FIG. 2H), a saddle 16 (see the isolated view of FIG. 2I) and only one insert 18 (see isolated view in FIG. 2J), in contrast to the pair of inserts 18 employed in the embodiment of FIGS. 1A-1J.

Fastener 12 includes an elongate shaft 22 having a proximal end and a distal end and a head 24 at the proximal end thereof. As shown, elongate shaft 22 is a screw shaft having threads 26 therealong. Head 24 includes a slot 28 that extends in a proximal-distal direction aligned with the longitudinal axis L-L.

The tulip 14 has a bore 32 therethrough that is dimensioned to allow the distal end of elongate shaft 12 to pass therethrough, but the dimension of the distal opening 32D is smaller than the largest cross-sectional dimension of the head 24, and thereby prevents passage of the head 24 therethrough, as illustrated in FIGS. 2A-2E. Insert 18 is fixed at 34 to tulip 14 as shown in FIG. 2E, so as to protrude into the bore 32. Slot 28 is configured and dimensioned to receive the protruding end of insert 18, to allow insert 18 to freely slide therein in the proximal distal direction, but to prevent movements in any other directions. Insert 18 may be fixed to tulip 14 by adhesives, welding, press fitting and/or other fixation expedients, preferably by press fitting into receptacle 34 formed in tulip 14. Slot 28 is formed to allow insert 18 to slide only in a proximal-distal direction that permits pivoting of the shaft 22 relative to the tulip 14 in one plane only. FIG. 2C shows a longitudinal sectional view of assembly 10 taken along line 2C-2C of FIG. 2A. FIGS. 2A-2C illustrate the assembly 10 where the fastener 12 is aligned with the longitudinal axis L-L of the assembly 10 and tulip 14. FIG. 2D shows the longitudinal sectional view of FIG. 2C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 2C. Saddle 16 has a concave distal surface 16S configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 2D. FIG. 2D illustrates a maximum angle 36 of pivoting in one direction, as insert 18 makes contact with the end of slot 28. As shown in FIG. 2E, insert 18 is centered in slot 28 when shaft 22 is aligned with the longitudinal axis L-L of the tulip 14. Alternatively, slot 28 could be asymmetrically formed so as to allow angulation 36 on one side of the longitudinal axis L-L to be greater than angulation on the other side (angulation the opposite direction).

In the embodiment shown, saddle 16 is a standard saddle and is configured and dimensioned to be retained by shoulder 14S when fitted into tulip 14, see FIG. 2H. The saddle-shaped tulip 14 further includes a slot 14ST passing therethrough, as shown in FIGS. 2A and 2G that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes, by locking down with the set screw in a manner described above.

All components 12,14,16 and 18 of assembly 10 are preferably made of titanium. Alternatively, one or more components may be made of alternative materials, the same as described above with regard to the previous embodiment. The uniplanar angulation of assembly 10 may vary, but preferably has a range of about eighty (80) degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The height 18H of insert 18 is about 1 mm to about 2 mm, typically about 1.5 mm. The length 18L of insert 18 is about 1.5 mm to about 3 mm, typically about 2.25 mm.

FIG. 3A is a plan view of a uniplanar surgical screw assembly 10 according to another embodiment of the present invention. FIG. 3B shows assembly 10 having been rotated about its longitudinal axis L-L by ninety degrees, relative to the view shown in FIG. 3A. The assembly 10 of the embodiment of FIGS. 3A-3I includes a fastener 12 (see the isolated view of FIG. 3G), a saddle-shaped tulip 14 (see the isolated view of FIG. 3H), and a saddle 16 (see the isolated view of FIG. 3I). Rather than employing one or more inserts 18, the embodiment of FIGS. 3A-3I provides protrusions 48 integrally formed with tulip 14 and protruding into the open space formed by the bore 32, as shown in FIGS. 3C-3F.

Fastener 12 includes an elongate shaft 22 having a proximal end and a distal end and a head 24 at the proximal end thereof. As shown, elongate shaft 22 is a screw shaft having threads 26 therealong. Head 24 includes a pair of slots 28 that extend in a proximal-distal direction aligned with the longitudinal axis L-L.

The tulip 14 has a bore 32 therethrough that is dimensioned to allow the distal end of elongate shaft 22 to pass therethrough, but the dimension of the distal opening 32D is smaller than the largest cross-sectional dimension of the head 24, and thereby prevents passage of the head 24 therethrough, as illustrated in FIGS. 3A-3E. Slots 28 are configured and dimensioned to receive the protruding ends of protrusions 48, to allow protrusions 48 to freely slide therein in the proximal distal direction, but to prevent movements in any other directions. As shown in FIGS. 3C-3F, slots 28 are formed diametrically opposite one another, separated by 180 degrees around the head 24. This is necessary to allow both protrusions 48 to slide in the same plane, resulting in an assembly that allows the elongate shaft 22 to pivot relative to the tulip 14 in one plane only. FIG. 3C shows a longitudinal sectional view of assembly 10 taken along line 3C-3C of FIG. 1A. FIGS. 3A-3C illustrate the assembly 10 where the fastener 12 is aligned with the longitudinal axis L-L of the assembly 10 and tulip 14. FIG. 3D shows the longitudinal sectional view of FIG. 3C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 3C. Saddle 16 has a concave distal surface 16S configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 3D. FIG. 3D illustrates a maximum angle 36 of pivoting, as protrusions 48 make contact with the ends of slots 28, respectively. As shown in FIG. 3E (enlarged view of the portion of FIG. 3C identified within circle 3E), protrusions 48 are centered in slots 28 when shaft 22 is aligned with the longitudinal axis L-L of the tulip 14. Alternatively, slots 28 could be asymmetrically formed so as to allow angulation 36 on one side of the longitudinal axis L-L to be greater than angulation on the other side (angulation in the opposite direction).

In the embodiment shown, saddle 16 is a standard saddle and is configured and dimensioned to be retained by shoulder 14S when fitted into tulip 14, see FIG. 3H. The saddle-shaped tulip 14 further includes a slot 14ST passing therethrough, as shown in FIGS. 3A and 3H that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes, such as in a manner already previously described.

All components 12,14,16 and 48 of assembly 10 are preferably made of titanium. Alternatively, one or more components may be made of one or more alternative materials such as described in regard to previous embodiments. The uniplanar angulation of assembly 10 may vary, but preferably has a range of about eighty (80) degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The height 48H of protrusion 48 is about 1 mm to about 2 mm, typically about 1.5 mm. The length 48L: of protrusion 48 is about 1.5 mm to about 3 mm, typically about 2.25 mm.

FIG. 4A is a plan view of a uniplanar surgical screw assembly 10 according to another embodiment of the present invention. FIG. 4B shows assembly 10 having been rotated about its longitudinal axis L-L by ninety degrees, relative to the view shown in FIG. 4A. The assembly 10 of the embodiment of FIGS. 4A-4I includes a fastener 12 (see the isolated view of FIG. 4G), a saddle-shaped tulip 14 (see the isolated view of FIG. 4H), a saddle 16 (see the isolated view of FIG. 4I) and only one protrusion 48 (see FIGS. 4C-4F), in contrast to the pair of protrusions 48 employed in the embodiment of FIGS. 3A-3I.

Fastener 12 includes an elongate shaft 22 having a proximal end and a distal end and a head 24 at the proximal end thereof. As shown, elongate shaft 22 is a screw shaft having threads 26 therealong. Head 24 includes a slot 28 that extends in a proximal-distal direction aligned with the longitudinal axis L-L.

The tulip 14 has a bore 32 therethrough that is dimensioned to allow the distal end of elongate shaft 12 to pass therethrough, but the cross-sectional dimension of the distal opening 32D is smaller than the largest cross-sectional dimension of the head 24, and thereby prevents passage of the head 24 therethrough, as illustrated in FIGS. 4A-4E. Protrusion 48 is integral with tulip 14 and protrudes into the bore 32, as illustrated in FIGS. 4C-4F. Slot 28 is configured and dimensioned to receive the protruding end of protrusion 48, to allow protrusion 48 to freely slide therein in the proximal distal direction, but to prevent movements in any other directions. Slot 28 is formed to allow protrusion 48 to slide only in a proximal-distal direction that permits pivoting of the shaft 22 relative to the tulip 14 in one plane only. FIG. 4C shows a longitudinal sectional view of assembly 10 taken along line 4C-4C of FIG. 4A. FIGS. 4A-4C illustrate the assembly 10 where the fastener 12 is aligned with the longitudinal axis L-L of the assembly 10 and tulip 14. FIG. 4D shows the longitudinal sectional view of FIG. 4C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 4C. Saddle 16 has a concave distal surface 16S configured and dimensioned as a bearing surface to allow the convex curvature of head 24 to slide relative thereto. Accordingly, as shaft 22 is pivots relative to tulip 14, head 24 rotates against bearing surfaces of the tulip 14 and saddle 16, as illustrated in FIG. 4D. FIG. 4D illustrates a maximum angle 36 of pivoting in one direction, as protrusion 48 makes contact with the end of slot 28. As shown in FIG. 4E, protrusion 48 is centered in slot 28 when shaft 22 is aligned with the longitudinal axis L-L of the tulip 14. Alternatively, slot 28 could be asymmetrically formed so as to allow angulation 36 on one side of the longitudinal axis L-L to be greater than angulation on the other side (angulation in the opposite direction).

In the embodiment shown, saddle 16 is a standard saddle and is configured and dimensioned to be retained by shoulder 14S when fitted into tulip 14, see FIG. 4H. The saddle-shaped tulip 14 further includes a slot 14ST passing therethrough, as shown in FIGS. 2A and 2G that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes, such as in a manner described in previous embodiments.

All components 12,14,16 and 18 of assembly 10 are preferably made of titanium. One or more components may be made of an alternative material, like described in previous embodiments. The uniplanar angulation of assembly 10 may vary, but preferably has a range of about eighty (80) degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The height 18H of insert 18 is about 1 mm to about 2 mm, typically about 1.5 mm. The length 18L of insert 18 is about 1.5 mm to about 3 mm, typically about 2.25 mm.

FIG. 5A is a plan view of a uniplanar surgical screw assembly 10, according to another embodiment of the present invention. FIG. 5E shows assembly 10 having been rotated about its longitudinal axis L-L by ninety degrees, relative to the view shown in FIG. 5A. The assembly 10 of the embodiment of FIGS. 5A-5J includes a fastener 12 (see the isolated view of FIG. 5G), a saddle-shaped tulip 14 (see the isolated view of FIG. 5H), a saddle 16 (see the isolated view of FIG. 5I) and a pair of flat inserts 58 (see isolated view of a flat insert 58 in FIG. 5J).

Fastener 12 includes an elongate shaft 22 having a proximal end and a distal end and a head 24 at the proximal end thereof. As shown, elongate shaft 22 is a screw shaft having threads 26 therealong. Head 24 includes a pair of flats 68 on an otherwise convex surface, typically an otherwise spherical surface. The surfaces of flats 68 are substantially parallel to one another as shown in FIGS. 5C-5D.

The tulip 14 has a bore 32 therethrough that is dimensioned to allow the distal end of elongate shaft 12 to pass therethrough, but the cross-sectional dimension of the distal opening 32D is smaller than the largest cross-sectional dimension of the head 24, and thereby prevents passage of the head 24 therethrough, as illustrated in FIGS. 5A-5B and 5D-5F. Flat inserts 58 are received in receptacles 64 formed in tulip 14 as shown in FIGS. 5C-5D, in an orientation, so that the flat surface 58F of flat insert 58 interfaces with flat 68 of head 24, as also shown in FIGS. 5C-5D. The interaction between the flats 68 and flat sides 58F prevents all pivoting of the shaft 22 relative to the tulip 14, except for in one plane, that plane being parallel to the flats 68 and flat sides 58F. The non-flat side of insert 58 is received in receptacle 64 which has a shape that mates with the non-flat side of the insert 58.

The non-flat side of insert 58 is shaped and configured to prevent the flat insert 58 from sliding relative to the receptacle 64. In the embodiment shown in FIG. 5J, the non-flat side comprises a proximal end portion 58P, a central portion 58C, and a distal end portion 58D, wherein the central portion 58C extends further from the flat side 58D than the distances by which the proximal 58P and distal 58D end portions extend from the flat side 58F. In the embodiment shown in FIG. 5J, the central portion has a first curvature and the proximal and distal end portions have a second curvature, the first curvature having a smaller radius of curvature than the second curvature. In the embodiment of FIG. 5J, the non-flat side includes a bulbous portion 58C extending further from the flat side than an extent to which a remainder (58Pm 58D) of the non-flat side extends from the flat side 58F.

Flat inserts 58 may be fixed to tulip 14 by adhesives, welding, press fitting and/or other fixation expedients, or loosely fit within tulip 14. As shown in FIGS. 5C-5D, flats 68 are formed diametrically opposite one another on head 24, so as to be parallel to one another. This is necessary to allow the flats 68 to rotate relative to the flat inserts 58 as shaft 22 is pivoted relative to tulip 14, such as is shown in FIG. 5F. Thus, flats 68 and flat surface 58F are all oriented in substantially parallel planes to maintain uniplanar movement of the shaft 22 relative to the tulip 14.

FIG. 5B shows a longitudinal sectional view of assembly 10 taken along line 5B-5B of FIG. 5E. FIGS. 5A-5C illustrate the assembly 10 where the fastener 12 is aligned with the longitudinal axis L-L of the assembly 10 and tulip 14. FIG. 5F shows the longitudinal sectional view of FIG. 5B, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 5D. Saddle 16 has a concave distal surface 16s configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 5F. FIG. 5F illustrates a maximum angle 36 of pivoting. The limits of pivoting are established by the shaft 22 contacting against the tulip 14.

In the embodiment shown, saddle 16 is a standard saddle and is configured and dimensioned to be retained by shoulder 14S when fitted into tulip 14, see FIG. 5h. The saddle-shaped tulip 14 further includes a slot 14ST passing therethrough, as shown in FIGS. 5B and 5H that is configured and dimensioned to receive an orthopedic rod or plate therein, in manners known in the art. Threading 14X allows a set screw (not shown) or the like to be torqued against the rod/plate to fix it relative to the tulip 14.

All components 12,14,16 and 58 of assembly 10 are preferably made of titanium. One or more components may be made of an alternative material such as described above. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The length 58L of insert 58 is about 4.5 mm to about 6.5 mm, typically about 5.3 mm.

FIG. 6A is a plan view of a uniplanar surgical screw assembly 10, according to another embodiment of the present invention. FIG. 6E shows assembly 10 having been rotated about its longitudinal axis L-L by ninety degrees, relative to the view shown in FIG. 6A. The assembly 10 of the embodiment of FIGS. 6A-6J includes a fastener 12 (see the isolated view of FIG. 6G), a saddle-shaped tulip 14 (see the isolated view of FIG. 6H), a saddle 16 (see the isolated view of FIG. 6I) and a single flat insert 58 (see isolated view of FIG. 5J).

Fastener 12 includes an elongate shaft 22 having a proximal end and a distal end and a head 24 at the proximal end thereof. As shown, elongate shaft 22 is a screw shaft having threads 26 therealong. Head 24 includes a flat 68 on an otherwise convex surface, typically an otherwise spherical surface. The surface of flat 68 is substantially parallel to the longitudinal axis L'-L' of the fastener 12, as shown in FIG. 6G.

The tulip 14 has a bore 32 therethrough that is dimensioned to allow the distal end of elongate shaft 22 to pass therethrough, but the cross-sectional dimension of the distal opening 32D is smaller than the largest cross-sectional dimension of the head 24, and thereby prevents passage of the head 24 therethrough, as illustrated in FIGS. 6A-6B and 6D-6F. Flat insert 58 is received in receptacle 64 formed in tulip 14 as shown in FIGS. 6C-6D, in an orientation, so that the flat surface 58F of flat insert 58 interfaces with flat 68 of head 24, as also shown in FIGS. 6C-6D. The interaction between the flat 68 and flat side 58F prevents all pivoting of the shaft 22 relative to the tulip 14, except for in one plane, that plane being parallel to the flat 68 and flat side 58F. The non-flat side of insert 58 is received in receptacle 64 which has a shape that mates with the non-flat side of the insert 58.

The non-flat side of insert 58 is shaped and configured to prevent the flat insert 58 from sliding relative to the receptacle 64. In the embodiment shown in FIG. 6J, the non-flat side comprises a proximal end portion 58P, a central portion 58C, and a distal end portion 58D, wherein the central portion 58C extends further from the flat side 58D than the distances by which the proximal 58P and distal 58D end portions extend from the flat side 58F. In the embodiment shown in FIG. 6J, the central portion has a first curvature and the proximal and distal end portions have a second curvature, the first curvature having a smaller radius of curvature than the second curvature. In the embodiment of FIG. 5J, the non-flat side includes a bulbous portion 58C extending further from the flat side than an extent to which a remainder (58Pm 58D) of the non-flat side extends from the flat side 58F.

Flat insert 58 may be fixed to tulip 14 by adhesives, welding, press fitting and/or other fixation expedients, or may be loosely fitted in tulip 14. As shown in FIGS. 6C-6D, the surface of flat 68 is parallel to the flat surface 58F. This is necessary to allow the flat 68 to rotate relative to the flat insert 58 as shaft 22 is pivoted relative to tulip 14, such as is shown in FIG. 6F. Thus, flat 68 and flat surface 58F are oriented in substantially parallel planes to maintain uniplanar movement of the shaft 22 relative to the tulip 14.

FIG. 6B shows a longitudinal sectional view of assembly 10 taken along line 6B-6B of FIG. 6E. FIGS. 6A-6C illustrate the assembly 10 where the fastener 12 is aligned with the longitudinal axis L-L of the assembly 10 and tulip 14. FIG. 6F shows the longitudinal sectional view of FIG. 6B, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 6D. Saddle 16 has a concave distal surface 16s configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 6F. FIG. 6F illustrates a maximum angle 36 of pivoting, as limited by the shaft contacting the tulip.

In the embodiment shown, saddle 16 is a standard saddle and is configured and dimensioned to be retained by shoulder 14S when fitted into tulip 14, see FIGS. 6F and 6H. The saddle-shaped tulip 14 further includes a slot 14ST passing therethrough, as shown in FIGS. 6E and 6H that is configured and dimensioned to receive an orthopedic rod or plate therein, in manners known in the art. Threading 14X allows a set screw (not shown) or the like to be torqued against the rod/plate to fix it relative to the tulip 14.

All components 12,14,16 and 58 of assembly 10 are preferably made of titanium. One or more components may be made of an alternative material, such as described above with regard to previous embodiments. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The length 58L of insert 58 is about 4.5 mm to about 6.5 mm, typically about 5.3 mm.

FIG. 7A is a plan view of a uniplanar surgical screw assembly 10, according to another embodiment of the present invention. FIG. 7B shows assembly 10 having been rotated about its longitudinal axis L-L by ninety degrees, relative to the view shown in FIG. 7A. The assembly 10 of the embodiment of FIGS. 7A-7I includes a fastener 12 (see the isolated view of FIG. 7G), a saddle-shaped tulip 14 (see the isolated view of FIG. 7H), and a saddle 16 (see the isolated view of FIG. 7I).

Fastener 12 includes an elongate shaft 22 having a proximal end and a distal end and a head 24 at the proximal end thereof. As shown, elongate shaft 22 is a screw shaft having threads 26 therealong. Head 24 includes a pair of protrusions 78 extending from diametrically opposite sides of a convex surface. Protrusions 78 may be inserts fixed to head 24, but are preferably integrally formed therewith.

The tulip 14 has a bore 32 therethrough that is dimensioned to allow the distal end of elongate shaft 12 to pass therethrough, but the cross-sectional dimension of the distal opening 32D is smaller than the largest cross-sectional dimension of the head 24, and thereby prevents passage of the head 24 therethrough, as illustrated in FIGS. 7A-7E. Slots 88 are formed in the inner surface of tulip 14 as shown in FIG. 7E. Slots 88 each extend in a proximal-distal direction and are formed diametrically opposite one another. Slots 88 are configured and dimensioned to receive the protruding ends of protrusions 78, to allow protrusions 78 to freely slide therein in the proximal-distal directions, but to prevent movements in any other directions, i.e., only uniplanar pivoting is allowed. As noted, protrusions 78 are preferably integral with head 24, but when fixed thereto, may be fixed to head 24 by adhesives, welding, press fitting and/or other fixation expedients, preferably by press fitting into receptacles formed in the head 24. As shown in FIGS. 7C-7F, slots 88 are formed diametrically opposite one another, separated by 180 degrees around the tulip 14. This is necessary to allow both protrusions 78 to slide in the same plane, resulting in an assembly that allows the elongate shaft 22 to pivot relative to the tulip 14 in one plane only. FIG. 7C shows a longitudinal sectional view of assembly 10 taken along line 7C-7C of FIG. 7A. FIGS. 7A-7C illustrate the assembly 10 where the fastener 12 is aligned with the longitudinal axis L-L of the assembly 10 and tulip 14. FIG. 7D shows the longitudinal sectional view of FIG. 7C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 1C. Saddle 16 has a concave distal surface 16S configured and dimensioned as a bearing surface to allow the convex curvature of head 24 to slide relative thereto. Additionally, in this embodiment, saddle 16 includes a pair of diametrically opposed notches in the bottom surface thereof that are configured and dimensioned to slidably fit over the protrusions 78.

As shaft 22 is pivoted relative to tulip 14, head 24 rotates against bearing surfaces of the tulip 14 and saddle 16, as illustrated in FIG. 7D. FIG. 7D illustrates a maximum angle 36 of pivoting, as protrusions 78 make contact with the ends of slots 88, respectively. As shown in FIG. 7E, protrusions 78 are centered in slots 88 when shaft 22 is aligned with the longitudinal axis L-L of the tulip 14. Alternatively, slots 88 could be asymmetrically formed so as to allow angulation 36 on one side of the longitudinal axis L-L to be greater than angulation on the other side (angulation in the opposite direction).

In the embodiment shown, saddle 16 is configured and dimensioned to be retained by shoulder 14S when fitted into tulip 14, see FIGS. 7E and 7H. The saddle-shaped tulip 14 further includes a slot 14ST passing therethrough, as shown in FIGS. 7A and 7H that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes.

All components 12,14,16 and 78 of assembly 10 are preferably made of titanium. One or more components may be made of an alternative material, like previous embodiments described above. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The height 78H of protrusion 78 is in the range from about 1 mm to about 3 mm, typically about 2 mm. The width 78W of protrusion 78 is within a range of from about 1 mm to about 2.5 mm, typically about 1.75 mm.

FIG. 8A is a plan view of a uniplanar surgical screw assembly 10, according to another embodiment of the present invention. FIG. 8B shows assembly 10 having been rotated about its longitudinal axis L-L by ninety degrees, relative to the view shown in FIG. 8A. The assembly 10 of the embodiment of FIGS. 8A-8I includes a fastener 12 (see the isolated view of FIG. 8G), a saddle-shaped tulip 14 (see the isolated view of FIG. 8H), and a saddle 16 (see the isolated view of FIG. 8I).

Fastener 12 includes an elongate shaft 22 having a proximal end and a distal end and a head 24 at the proximal end thereof. As shown, elongate shaft 22 is a screw shaft having threads 26 therealong. Head 24 includes a single protrusion 78 extending from a side of a convex surface thereof. Protrusion 78 may be an insert fixed to head 24, but is preferably integrally formed therewith.

The tulip 14 has a bore 32 therethrough that is dimensioned to allow the distal end of elongate shaft 22 to pass therethrough, but the cross-sectional dimension of the distal opening 32D is smaller than the largest cross-sectional dimension of the head 24, and thereby prevents passage of the head 24 therethrough, as illustrated in FIGS. 8A-8E. A slot 88 is formed in the inner surface on one side of the tulip 14 as shown in FIG. 8E. Slot 88 extends in a proximal-distal direction and is formed in a direction parallel to the longitudinal axis L-L. Slot 88 is configured and dimensioned to receive the protruding end of protrusion 78, to allow protrusion 78 to freely slide therein in the proximal-distal directions, but to prevent movements in any other directions, i.e., only uniplanar pivoting is allowed. As noted, protrusion 78 is preferably integral with head 24, but when fixed thereto, may be fixed to head 24 by adhesives, welding, press fitting and/or other fixation expedients, preferably by press fitting into receptacles formed in the head 24. As shown in FIGS. 8C-8F, slot 88 is formed to receive protrusion 78 therein, to allow protrusion 78 to slide in a plane, resulting in an assembly that allows the elongate shaft 22 to pivot relative to the tulip 14 in one plane only. FIG. 8C shows a longitudinal sectional view of assembly 10 taken along line 8C-8C of FIG. 8A. FIGS. 8A-8C illustrate the assembly 10 where the fastener 12 is aligned with the longitudinal axis L-L of the assembly 10 and tulip 14. FIG.

8D shows the longitudinal sectional view of FIG. 8C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 8C. Saddle 16 has a concave distal surface 16S configured and dimensioned as a bearing surface to allow the convex curvature of head 24 to slide relative thereto. Additionally, in this embodiment, saddle 16 includes a notch 90 in the bottom surface thereof that is configured and dimensioned to slidably fit over the protrusion 78.

As shaft 22 is pivoted relative to tulip 14, head 24 rotates against bearing surfaces of the tulip 14 and saddle 16, as illustrated in FIG. 8D. FIG. 8D illustrates a maximum angle 36 of pivoting, as protrusion 78 makes contact with the end of slot 88. As shown in FIG. 8E, protrusion 78 is centered in slot 88 when shaft 22 is aligned with the longitudinal axis L-L of the tulip 14. Alternatively, slot 88 could be asymmetrically formed so as to allow angulation 36 on one side of the longitudinal axis L-L to be greater than angulation on the other side (angulation in the opposite direction).

In the embodiment shown, saddle 16 is configured and dimensioned to be retained by shoulder 14S when fitted into tulip 14, see FIGS. 8E and 8H. The saddle-shaped tulip 14 further includes a slot 14ST passing therethrough, as shown in FIGS. 8A and 8H that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes.

All components 12,14,16 and 78 of assembly 10 are preferably made of titanium. One or more components may be made of an alternative material such as described above with regard to previous embodiments. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The height 78H of protrusion 78 is in the range from about 1 mm to about 3 mm, typically about 2 mm. The width 78W of protrusion 78 is within a range of from about 1 mm to about 2.5 mm, typically about 1.75 mm.

FIG. 9A is a plan view of a uniplanar surgical screw assembly 10 according to another embodiment of the present invention. FIG. 9B shows assembly 10 having been rotated about its longitudinal axis L-L by ninety degrees, relative to the view shown in FIG. 9A. The assembly 10 of the embodiment of FIGS. 9A-9I includes a fastener 12 (see the isolated view of FIG. 9G), a saddle-shaped tulip 14 (see the isolated view of FIG. 9H), and a saddle 16 (see the isolated view of FIG. 9I). Rather than employing one or more inserts 18, the embodiment of FIGS. 9A-9I provides protrusions 98 integrally formed with saddle 16 and protruding inwardly, see FIGS. 9E, 9F and 9I.

Fastener 12 includes an elongate shaft 22 having a proximal end and a distal end and a head 24 at the proximal end thereof. As shown, elongate shaft 22 is a screw shaft having threads 26 therealong. Head 24 includes a pair of slots 108 that extend in a proximal-distal direction aligned with the longitudinal axis L-L.

The tulip 14 has a bore 32 therethrough that is dimensioned to allow the distal end of elongate shaft 22 to pass therethrough, but the cross-sectional dimension of the distal opening 32D is smaller than the largest cross-sectional dimension of the head 24, and thereby prevents passage of the head 24 therethrough, as illustrated in FIGS. 9A-9E. Slots 28 are configured and dimensioned to receive the protruding ends of protrusions 98, to allow protrusions 98 to freely slide therein in the proximal-distal direction, but to prevent movements in any other directions. As shown in FIGS. 9C-9F, slots 28 are formed diametrically opposite one another, separated by 180 degrees around the head 24. This is necessary to allow both protrusions 98 to slide in the same plane, resulting in an assembly that allows the elongate shaft 22 to pivot relative to the tulip 14 in one plane only. FIG. 9C shows a longitudinal sectional view of assembly 10 taken along line 9C-9C of FIG. 9A. FIGS. 9A-9C illustrate the assembly 10 where the fastener 12 is aligned with the longitudinal axis L-L of the assembly 10 and tulip 14. FIG. 9D shows the longitudinal sectional view of FIG. 9C, but after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 9C. Saddle 16 has a concave distal surface 16S configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 9D. FIG. 9D illustrates a maximum angle 36 of pivoting, as protrusions 98 make contact with the ends of slots 208, respectively. As shown in FIG. 9E (enlarged view of the portion of FIG. 9C identified within circle 9E), protrusions 98 are centered in slots 208 when shaft 22 is aligned with the longitudinal axis L-L of the tulip 14. Alternatively, slots 108 could be asymmetrically formed so as to allow angulation 36 on one side of the longitudinal axis L-L to be greater than angulation on the other side (angulation in the opposite direction).

In the embodiment shown, saddle 16 is configured and dimensioned to be retained by shoulder 14S when fitted into tulip 14, see FIGS. 9E and 9H. The saddle-shaped tulip 14 further includes a slot 14ST passing therethrough, as shown in FIGS. 9A and 9H that is configured and dimensioned to receive an orthopedic rod or plate therein, in manners known in the art. Threading 14X allows a set screw (not shown) or the like to be torqued against the rod/plate to fix it relative to the tulip 14. The saddle 16 is configured to apply compression to the head 24 to lock an orientation of the fastener 12 relative to the tulip 14, thereby even preventing the movement in the one plane that is otherwise allowed, and thus preventing movement in all planes.

All components 12,14 and 16 of assembly 10 are preferably made of titanium. Alternatively, one or more components may be made of an alternative material, like previous embodiments described. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The height 18H of insert 18 is about 1 mm to about 2 mm, typically about 1.5 mm. The length 18L: of insert 18 is about 1.5 mm to about 3 mm, typically about 2.25 mm.

FIG. 11A is a plan view of a uniplanar surgical screw assembly 10, according to another embodiment of the present invention. FIG. 11B shows assembly 10 having been rotated about its longitudinal axis L-L by ninety degrees, relative to the view shown in FIG. 11A. The assembly 10 of the embodiment of FIGS. 11A-11IJ includes a fastener 12 (see the isolated view of FIG. 11I), a saddle-shaped tulip 14 (see the isolated view of FIG. 11G), and a saddle 16 (see the isolated view of FIG. 11H).

Fastener 12 includes an elongate shaft 22 having a proximal end and a distal end and a head 24 at the proximal end thereof. As shown, elongate shaft 22 is a screw shaft having threads 26 therealong. Head 24 includes a pair of opposing flats 68 on an otherwise convex surface, typically an otherwise spherical surface. The surfaces of flats 68 are substantially parallel to one another as shown in FIG. 11F.

The tulip 14 has a bore 32 therethrough that is dimensioned to allow the distal end of elongate shaft 12 to pass therethrough, but the cross-sectional dimension of the distal opening 32D is smaller than the largest cross-sectional dimension of the head 24, and thereby prevents passage of the head 24 therethrough, as illustrated in FIGS. 11A-11E. Saddle 16 includes a pair of opposing flats 158 (see FIG. 11H) that interface with flats 68 (see FIG. 11F). Saddle 16 is rotationally fixed relative to tulip 14 when assembly 10 is assembled (see FIG. 11E). The interface between flats 158 and flats 68, combined with the prevention of saddle 16 from rotating relative to tulip 14, prevents all pivoting of the shaft 22 relative to the tulip 14, except for in one plane, that plane being parallel to the flats 68 and flats 158.

FIG. 11C shows a longitudinal sectional view of assembly 10 taken along line 11C-11C of FIG. 11B. FIGS. 11A-11C illustrate the assembly 10 where the fastener 12 is aligned with the longitudinal axis L-L of the assembly 10 and tulip 14. FIG. 11D shows the assembly 10 after uniplanar pivoting of fastener 12/shaft 22 relative to tulip 14 by an angle 36 (as shown by the angle 36 between the longitudinal axis L'-L' of the fastener 12 and the longitudinal axis L-L of the tulip 14.

Saddle 16 is configured and dimensioned to be fixed relative to tulip 14 while abutting the proximal portion of head 24 as shown in FIG. 11E. Saddle 16 has a concave distal surface 16s configured and dimensioned as a bearing surface to allow the convex curvature of head 24 to slide relative thereto. Accordingly, as shaft 22 is pivoted relative to tulip 14, head 24 rotates against bearing surfaces of the tulip 14 and saddle 16, as illustrated in FIG. 11D. FIG. 11D illustrates a maximum angle 36 of pivoting. The limits of pivoting are established by the shaft 22 contacting against the tulip 14.

In the embodiment shown, the saddle-shaped tulip 14 includes a slot 14ST passing therethrough, as shown in FIGS. 11A and 11C that is configured and dimensioned to receive an orthopedic rod or plate therein, in manners known in the art (an example of which is shown in FIG. 10). Threading 14X allows a set screw 46 (see FIG. 10) or the like to be torqued against the rod/plate to fix it relative to the tulip 14.

All components 12,14 and 16 of assembly 10 are preferably made of titanium. One or more components may be made of an alternative material such as described above. The uniplanar angulation of assembly 10 may vary, but preferably has a range of about 80 degrees (twice angle 36). The dimensions of the components will vary depending upon the location of the spine in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length of shaft 22 typically falls within a range of about 10 mm to about 100 mm. The length of flat 158 is about 4.5 mm to about 6.5 mm, typically about 5.0 mm.

FIG. 11J is a proximal end view of the assembly of FIG. 11B illustrating a tool interface 16T that can be interfaced by a tool to drive the fastener 12 into the bone. The present invention is not limited to this type of interface as any other equivalent type of torquing interface could be used.

FIG. 12A is a plan view of a surgical screw assembly 10, according to another embodiment of the present invention. In the embodiment of FIG. 12A, the surgical screw assembly is a polyaxial surgical screw assembly, meaning that, in an unlocked condition, shaft 22 can pivot relative to tulip 14 in any plane. However, the locking force augmentation features (e.g., the step features, arrangement and functioning of the tulip and head, and methods of providing enhanced locking force) as described with this embodiment are equally applicable to uniplanar surgical screw assemblies, such as those described above, as well as screw assemblies that can pivot in multiple planes, but not all planes, and are generally applicable to all polyaxial and uniplanar screw assemblies to provide enhanced locking force. FIG. 12B is a longitudinal sectional view of the assembly 10 taken along line 12B-12B in FIG. 12A. FIG. 12C is a perspective view of the assembly 10 of FIG. 12A.

The assembly 10 of the embodiment of FIGS. 12A-12G includes a fastener 12 including an elongate shaft 22 and a head 24 at a proximal end of the shaft 22. As shown, elongate shaft 22 is a screw shaft having threads 26 therealong. Head 24 is substantially spherical, having a convex external surface. A tulip 14 has a bore 32 therethrough that defines a bearing surface against which head 24 can rotate when assembly 10 is in an unlocked configuration. Bore 32 is dimensioned to allow the distal end of elongate shaft 12 to pass therethrough as well as to allow the head 24 to be inserted into the tulip 14.

FIG. 12D is an enlarged detailed view of the portion of FIG. 12B within circle 12D. A first step feature 40 is located at a distal end portion of bore 32 and extends inwardly therefrom. The first step feature 40 reduces the diameter 38 of bore 32 to a dimension 42 that allows the distal end of the elongate shaft to pass therethrough, and allows all of the shaft 22 to pass therethrough, but prevents passage of head 24 therethrough as a portion of the first step feature contacts the external surface of the head, as shown in FIG. 12D. A second step feature 50 is located at a distal end portion of bore 32, distally of first step feature 40. Second step feature 50 further reduces the diameter of bore 32 to a dimension 52 less than dimension 42 established by first step feature, the further reduced dimension 52 allowing the distal end of the elongate shaft 22 to pass therethrough, and allows all of the shaft 22 to pass therethrough, but prevents passage of head 24 therethrough.

FIG. 12D illustrates the assembly in an unlocked configuration. In an unlocked configuration, as noted above, head 24 can be rotated relative to tulip 14 so as to pivot the shaft 22 relative to the longitudinal axis L-L of the tulip 14. As also noted above, in this embodiment, shaft 22 can be pivoted in any plane when assembly 10 is in an unlocked configuration. However, the step features described with regard to this embodiment can be likewise installed in a uniplanar assembly, wherein, in an unlocked configuration, shaft 22 would be allowed to pivot in a single plane only.

FIG. 12E is a top view of the assembly 10 of FIG. 12A. A tool interface 16T is provided in the proximal end of head 24 that can be interfaced by a tool to drive the fastener 12 into the bone. The present invention is not limited to this type of interface as any other equivalent type of torquing interface could be used.

In the unlocked configuration shown in FIGS. 12B and 12D, the external surface of head 24 contacts the first step feature 40. In a preferred embodiment, the external surface of head 24 does not contact the second step feature 50, as shown in FIG. 12D. Alternatively, step feature 50 may be configured to extend further into the bore 32 so that the external surface of head 24 contacts both the first and second step features when in an unlocked configuration.

Figure 12G:
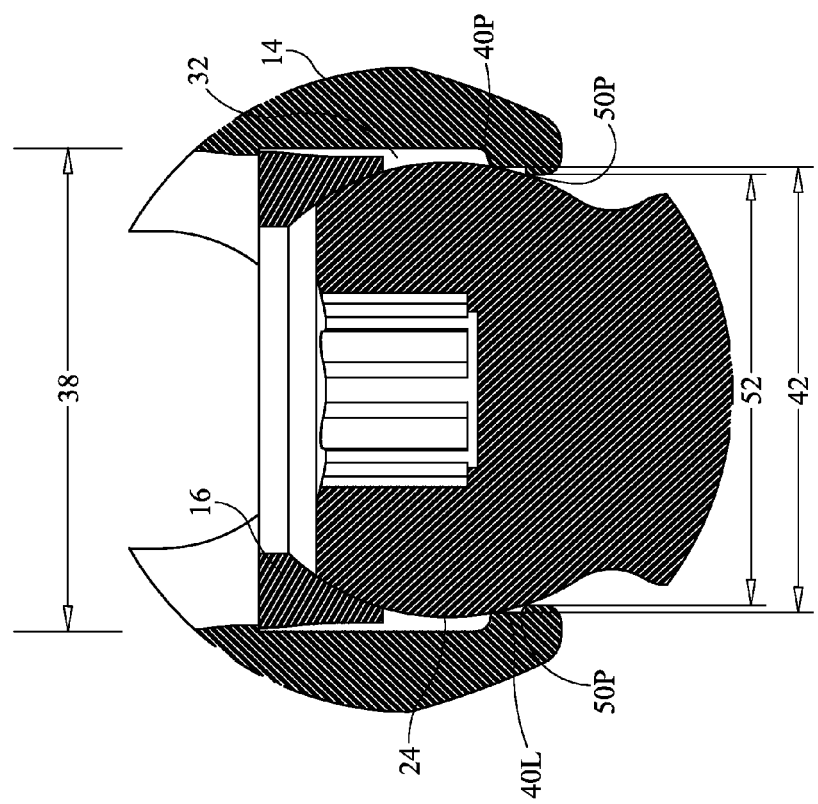
FIG. 12G is an enlarged detailed view of the portion of FIG. 12F within circle 12G.
Figure 12F:
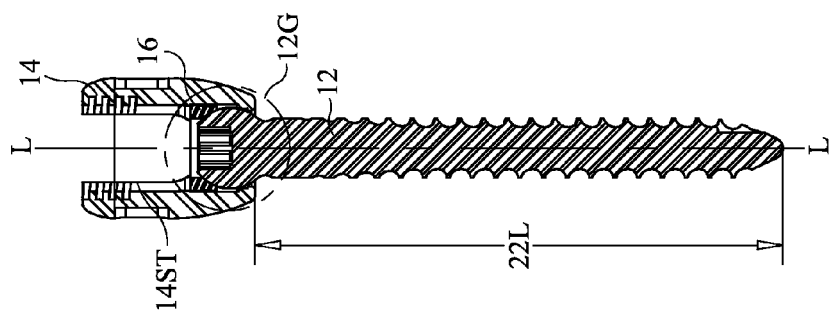
FIG. 12F is a longitudinal sectional view of the assembly of FIG. 12A, similar to that shown in FIG. 12B, but when the assembly is in a locked configuration.

FIG. 12F is a longitudinal sectional view of the assembly 10, similar to that shown in FIG. 12B, but when the assembly 10 is in a locked configuration. FIG. 12G is an enlarged detailed view of the portion of FIG. 12F within circle 12G. When in a locked configuration the external surface of the head 24 contacts both first step feature 40 and second step feature 50. To establish a locked configuration, a compression force is established between head 24 and step features 40, 50. This is typically accomplished by applying force in a distal direction to the proximal end of head 24 while holding tulip 14 relatively stationary, applying force to tulip 14 in a proximal direction while holding head 24 relatively stationary, or most typically, applying force to head 24 in a distal direction while drawing tulip 14 in a proximal direction. Upon application of sufficient force (typically in the range of about 7.5 Nm to about 12.5 Nm, more typically in the range of about 9.5 Nm to 10.5 Nm, although the preferred force may vary depending upon the dimensions of the components and the materials from which they are made, for example) the external surface of the head 24 and step features 40, 50 engage one another such that at least one of a portion of the external surface of the head 24 contacting the step feature 40 and step feature 40 deforms and typically a cold welding is performed, while at least frictional contact is established between the external surface of the head 24 and step feature 50 is established. Preferably, at least one of a portion of the external surface of the head 24 contacting step feature 50 and step feature 50 also deforms and established cold welding. This results in locking head 24 relative to tulip 14, thereby preventing movements of head 24 relative to tulip 14.

It is possible, if necessary to unlock the assembly 10 after a locking condition has been established. This can be accomplished by removal of the compression force, after which a tool can be inserted into bore 32 to pry tulip 14 free from head 24, thereby breaking the cold welds, or by any other technique that breaks the cold welds, such as by proximal movement of head 24 relative to tulip 14 or distal movement of tulip 14 relative to head 24.

Figure 12I:
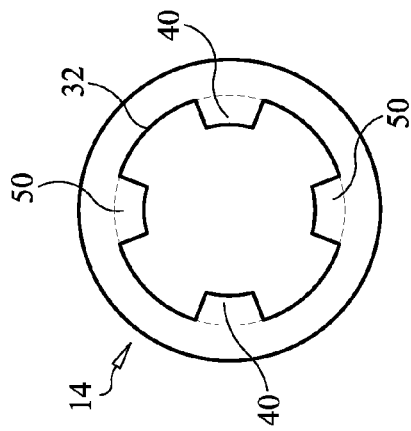
FIGS. 12H-12L illustrate various arrangements of first and second step features according to embodiments of the present invention.
Figure 12H:
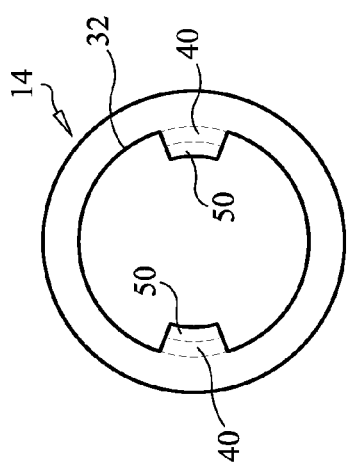
Figure 12K:
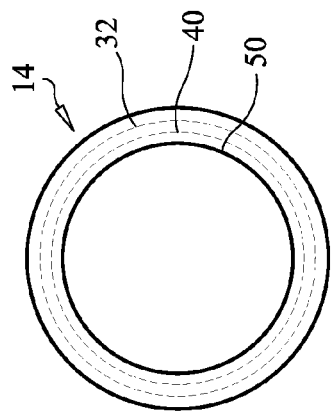
Figure 12J:
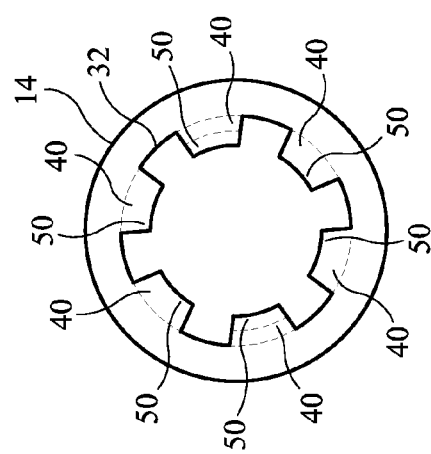
Figure 12L:
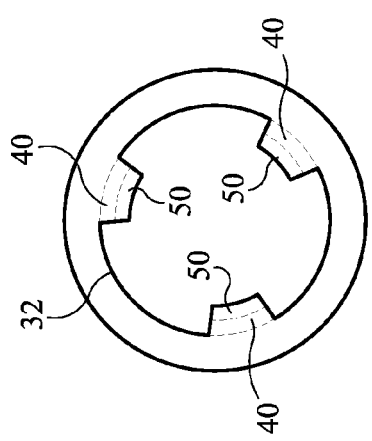

Preferably step features 40 and 50 extend continuously about the entire inner circumference of bore 32 as illustrated in the schematic distal end view of tulip 14. Alternatively, step features 40 and 50 may be discontinuously provided in various arrangements. FIG. 12I illustrates an arrangement in which a pair of step features 40 and a pair of step features 50 extend from bore 32 and are diametrically opposed with one another, with step features 40 and 50 being aligned with one another in the longitudinal axis direction. FIG. 12J illustrates an arrangement in which a pair of step features 40 and a pair of step features 50 extend from bore 32 and are diametrically opposed with one another, with step features 40 and 50 being offset to one another by ninety degrees. FIG. 12K illustrates an arrangement in which a three step features 40 are equidistantly spaced about the circumference of bore 32 and three step features 50 are equidistantly spaced about the circumference of bore 32, with respective features 40 and 50 being aligned in the longitudinal direction. Alternatively, features 40 may be offset from features 50 when viewed in the direction of the longitudinal axis L-L. FIG. 12L illustrates an arrangement in which a pair of first step features 40 are diametrically opposed and six second step features 50 are equidistantly spaced about the circumference of bore 32. Likewise, an embodiment could be provided with two step features 50 and six step features 40. Further alternatively to continuous step features 40 and 50, any number of discontinuous first step features 40 and any number of discontinuous second step features 50 may be provided, with any circumferential positioning (relative to the circumference of bore 32) desired. Also, the step features 40 may be aligned longitudinally with the step features 50 and/or staggered.

Referring now back to FIGS. 12D and 12G, a preferred configuration of the first and second step features 40,50 is described. A proximal end portion 40P that extends from the bore 32 is the portion of the step feature 40 that contacts the external surface of the head 24 and deforms and/or is deformed by head 24 during locking. Likewise, proximal end portion 50P that extends from the bore 32 is the portion of the step feature 50 that contacts the external surface of the head 24 during locking and, in embodiments where deformation takes place, deforms and/or is deformed by head 24 during locking. A longitudinal surface 40L of first step feature 40 extends distally away from proximal end portion 40P and preferably extends tangentially and distally away from the external surface of head 24 when proximal portion 40P contacts the external surface of the head 24. Alternatively, the longitudinal surface 40L may extend away from the external surface of the head 24 at some other angle, but preferably does not contact the external surface of the head 24 even in the locked configuration. A longitudinal surface SOL of second step feature 50 extends distally away from proximal end portion 50P and preferably extends tangentially and distally away from the external surface of head 24 when proximal portion 50P contacts the external surface of the head 24. Alternatively, the longitudinal surface SOL may extend away from the external surface of the head 24 at some other angle, but preferably does not contact the external surface of the head 24 even in the locked configuration.

Referring to FIGS. 12B, 12C and 12F, the tulip 14 includes a slot extending therethrough normal to the longitudinal axis L-L of bore 32. Slot 14ST is configured and dimensioned to receive a rod, shaft, plate or channel for connection to assembly 10. A saddle 16 is configured and dimensioned to be fitted in the bore 32 of tulip 14 against the head 24 to prevent the head 24 from moving proximally relative to the tulip 14. Saddle 16 is configured and dimensioned to be fixed relative to tulip 14 while abutting the proximal portion of head 24. Saddle 16 has a concave distal surface 16S configured and dimensioned as a bearing surface to allow the convex curvature of head 24 to slide relative thereto. Accordingly, as shaft 22 is pivoted relative to tulip 14, head 24 rotates against bearing surfaces of the tulip 14/bore 32 and saddle 16. The limits of pivoting are established by the shaft 22 contacting against the tulip 14. Threading 14X in tulip 14 allows a set screw 46 (see FIG. 10) or other driving member to be torqued or otherwise driven against the rod, shaft, plate or channel to fix it relative to the tulip 14, and also to apply force to the saddle 16, which in turn drives compression of the head 24 relative to the step features 40, 50 to established a locked configuration. Thus, the saddle 16 is configured to apply compression to the head 24 to lock an orientation of the fastener 12 relative to the tulip 14, by driving the external surface of the head 24 against the first and second step features 40, 50.

All components 12, 14, 16, 40 and 50 of assembly 10 are preferably made of titanium. One or more components may be made of an alternative material such as cobalt chromium alloys, stainless steel, or any of the other alternative materials described above. The step features 40 and 50 are preferably integrally made with the tulip 14, such as by machining metal sintering, direct metal deposition or casting. Alternatively, the step features 40, 50 can be integrally attached to the tulip to extend from the bore 32 in the manners described, by welding, or some other permanent attachment method that will not release even when the proximal portions of the step features 40, 50 are plastically deformed under the compression forces. The dimensions of the components will vary depending upon the location of the spine (or elsewhere in the body) in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length 22L of shaft 22 typically falls within a range of about 10 mm to about 100 mm. The inside diameter 38 of bore 32 is typically within the range of about 3 mm to about 11.5 mm. The inside diameter 38 in the embodiment shown in FIG. 12D is about 8.1 mm and the inside diameter 38 in the embodiment shown in FIG. 12G is about 9.6 mm. The outside diameter of head 24 is typically within the range of about 2.5 mm to about 11.5 mm. The outside diameter of head 24 in the embodiment shown in FIG. 12D is about 7.5 mm and the outside diameter of head 24 in the embodiment shown in FIG. 12G is about 9 mm. Dimension 52 is typically in the range of about 5 mm to about 10 mm, more typically in the range of about 6 mm to about 9 mm. In one preferred embodiment, dimension 52 was about 7.05 mm. In another preferred embodiment, dimension 52 was about 8.55 mm. Dimension 42 is typically in the range of about 5.3 mm to about 10.3 mm, more typically in the range of about 6.3 mm to about 9.3 mm. However, the dimensions 42 and 52 may vary from these ranges, as dimensions of 38 and the outside diameter of head 24 vary. In one preferred embodiment, where dimension 52 was about 7.05 mm, dimension 42 was about 7.35 mm. In another preferred embodiment, where dimension 52 was about 8.55 mm, dimension 42 was about 8.85 mm. The tolerance between head 24 and bore 32 is typically in the range of about 0.3 mm to about 0.9 mm. The tolerance in the embodiments of FIGS. 12D and 12G is about 0.6 mm±0.05 mm.

FIG. 13A is a plan view of a surgical screw assembly 10, according to another embodiment of the present invention. In the embodiment of FIG. 13A, the surgical screw assembly is a polyaxial surgical screw assembly, meaning that, in an unlocked condition, shaft 22 can pivot relative to tulip 14 in any plane. However, the locking force augmentation features (e.g., the step features, arrangement and functioning of the tulip and head, and methods of providing enhanced locking force) as described with this embodiment are equally applicable to uniplanar surgical screw assemblies, such as those described above, as well as screw assemblies that can pivot in multiple planes but not all planes, and generally to all polyaxial and uniplanar screw assemblies to provide enhanced locking force. FIG. 13B is a longitudinal sectional view of the assembly 10 taken along line 13B-13B in FIG. 13A. FIG. 13C is a perspective view of the assembly 10 of FIG. 13A.

The assembly 10 of the embodiment of FIGS. 13A-13G includes a fastener 12 including an elongate shaft 22 and a head 24 at a proximal end of the shaft 22. As shown, elongate shaft 22 is a screw shaft having threads 26 therealong. Head 24 is substantially spherical, having a convex external surface. A tulip 14 has a bore 32 therethrough that defines a bearing surface against which head 24 can rotate when assembly 10 is in an unlocked configuration. Bore 32 is dimensioned to allow the distal end of elongate shaft 12 to pass therethrough as well as to allow the head 24 to be inserted into the tulip 14.

FIG. 13D is an enlarged detailed view of the portion of FIG. 13B within circle 13D. A first step feature 40 is located at a distal end portion of bore 32 and extends inwardly therefrom. The first step feature 40 reduces the diameter 38 of bore 32 to a dimension 42 that allows the distal end of the elongate shaft to pass therethrough, and allows all of the shaft 22 to pass therethrough, but prevents passage of head 24 therethrough as a portion of the first step feature contacts the external surface of the head, as shown in FIG. 13D. A second step feature 50 is located at a distal end portion of bore 32, distally of first step feature 40. Second step feature 50 further reduces the diameter of bore 32 to a dimension 52 less than dimension 52 established by first step feature, the further reduced dimension 52 allowing the distal end of the elongate shaft 22 to pass therethrough, and allows all of the shaft 22 to pass therethrough, but prevents passage of head 24 therethrough. Third step feature 60 further reduces the diameter of bore 32 to a dimension 62 less than dimension 52 established by second step feature, the further reduced dimension 62 allowing the distal end of the elongate shaft 22 to pass therethrough, and allowing all of the shaft 22 to pass therethrough, but preventing passage of head 24 therethrough.

FIG. 13D illustrates the assembly in an unlocked configuration. In an unlocked configuration, as noted above, head 24 can be rotated relative to tulip 14 so as to pivot the shaft 22 relative to the longitudinal axis L-L of the tulip 14. As also noted above, in this embodiment, shaft 22 can be pivoted in any plane when assembly 10 is in an unlocked configuration. However, the step features described with regard to this embodiment can be likewise installed in a uniplanar assembly, wherein, in an unlocked configuration, shaft 22 would be allowed to pivot in a single plane only; or in an otherwise limited assembly, such as an assembly allowing pivoting in more than one plane, but not all planes.

FIG. 13E is a top view of the assembly 10 of FIG. 13A. A tool interface 16T is provided in the proximal end of head 24 that can be interfaced by a tool to drive the fastener 12 into the bone. The present invention is not limited to this type of interface as any other equivalent type of torquing interface could be used.

Figure 13R:
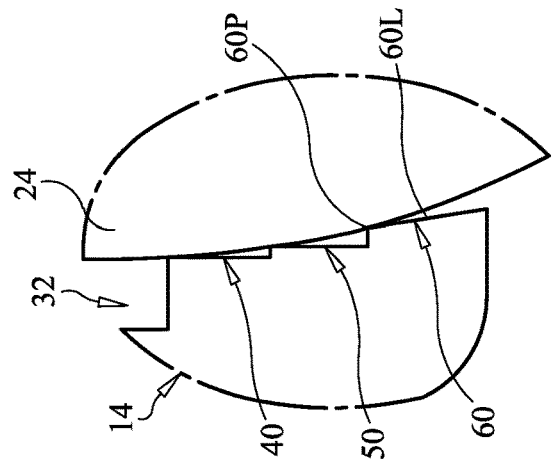
FIG. 13A is a plan view of a surgical screw assembly in an unlocked configuration according to another embodiment of the present invention.
FIG. 13B is a longitudinal sectional view of the assembly of FIG. 13A taken along line 13B-13B.
FIG. 13C is a perspective view of the assembly shown in FIG. 13A.
FIG. 13D is an enlarged detailed view of the portion of FIG. 13B within circle 13D.
FIG. 13E is a proximal end view of the assembly of FIG. 13A.
FIG. 13F is an enlarged detailed view of the portion of FIG. 13D within ellipse 13F.
FIG. 13G is a plan view of the surgical screw assembly of FIG. 13A in a provisionally locked configuration according to an embodiment of the present invention.
FIG. 13H is a longitudinal sectional view of the assembly of FIG. 13B taken along line 13H-13H.
FIG. 13I is a perspective view of the assembly shown in FIG. 13G.
FIG. 13J is an enlarged detailed view of the portion of FIG. 13H within circle 13J.
FIG. 13K is a proximal end view of the assembly of FIG. 13G.
FIG. 13L is an enlarged detailed view of the portion of FIG. 13J within ellipse 13L.
FIG. 13M is a plan view of the surgical screw assembly of FIGS. 13A and 13G in a fully locked configuration according to an embodiment of the present invention.
FIG. 13N is a longitudinal sectional view of the assembly of FIG. 13M taken along line 13N-13N.
FIG. 13O is a perspective view of the assembly shown in FIG. 13M.
FIG. 13P is an enlarged detailed view of the portion of FIG. 13N within circle 13P.
Figure 13L:
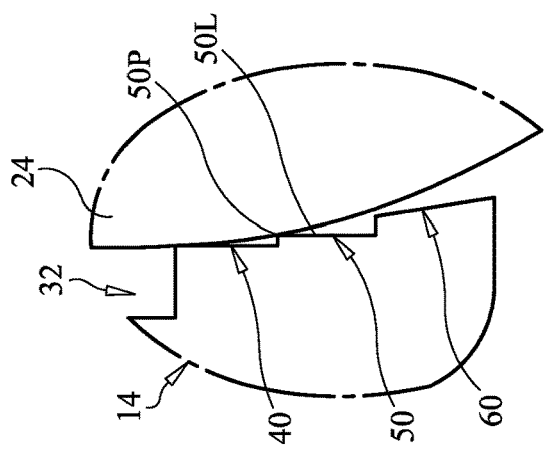
Figure 13F:
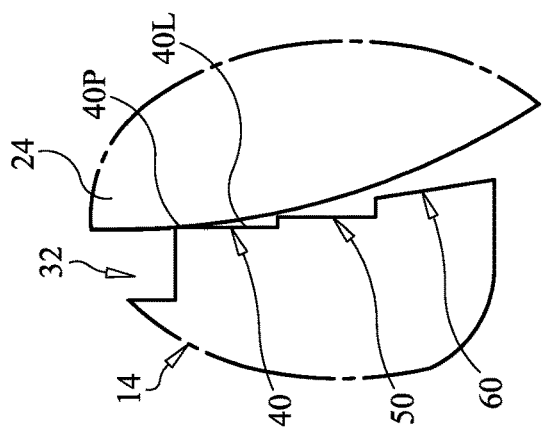

In the unlocked configuration shown in FIGS. 13B and 13D, the external surface of head 24 contacts the first step feature 40, see the enlarged partial view in FIG. 13F, taken of the portion of FIG. 13D within ellipse 13F. In a preferred embodiment, the external surface of head 24 does not contact the second step feature 50 or the third step feature 60, as shown in FIG. 13F. Alternatively, step feature 50 may be configured to extend further into the bore 32 so that the external surface of head 24 contacts both the first and second step features 40, 50 when in an unlocked configuration. Further alternatively, step features 50 and 60 may be configured to extend further into the bore 32 so that the external surface of head 24 contacts first step feature 40, second step feature 50 and third step feature 60 when in an unlocked configuration. However, in these alternative arrangements, final locking would be even more enhanced relative to the embodiment described in FIG. 13F.

FIGS. 13G-13K correspond to FIGS. 13A-13E, except that the assembly s shown in a provisionally locked configuration. FIG. 13H is a longitudinal sectional view of the assembly 10 taken along line 13H-13H in the plan view of FIG. 13G. FIG. 13I is a perspective view of the assembly 10 shown in FIG. 13G. FIG. 13J is an enlarged detailed view of the portion of FIG. 13H within circle 13J. When in a provisionally locked configuration the external surface of the head 24 contacts both first step feature 40 and second step feature 50, but preferably not step feature 60, as shown in FIG. 13L.

Figure 13P:
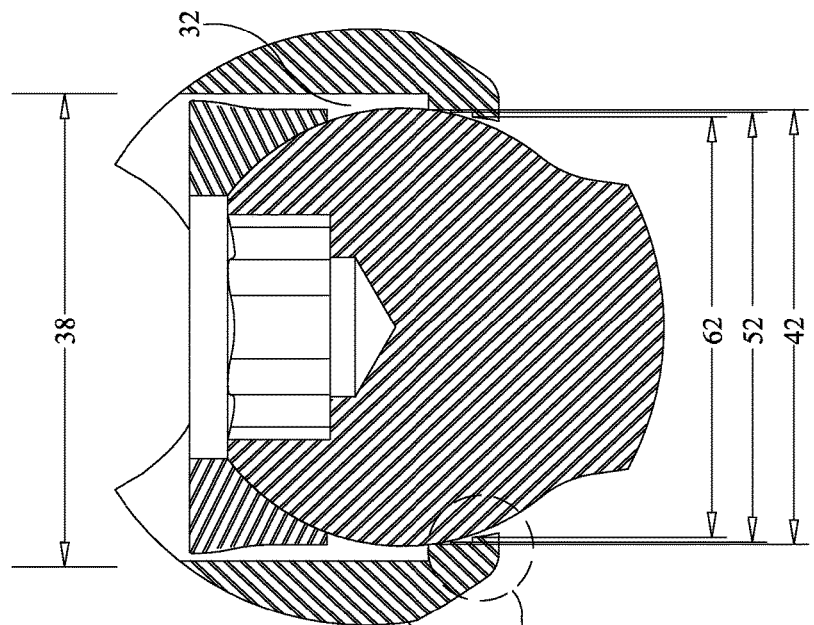
Figure 13O:
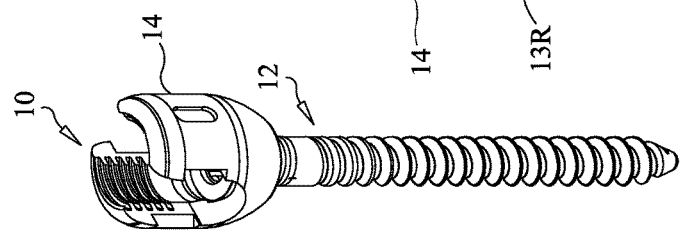
Figure 13Q:
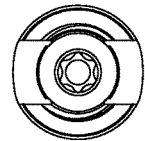
Figure 13N:
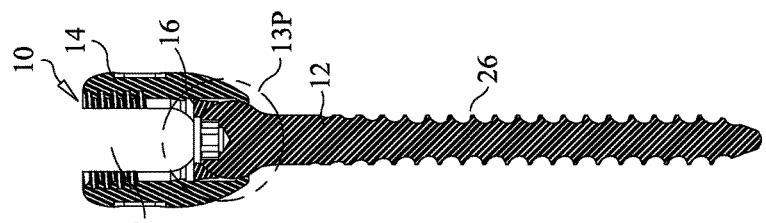

FIGS. 13M-13Q correspond to FIGS. 13A-13E and 13G-13K, respectively, except that the assembly is shown in a finally locked configuration. FIG. 13N is a longitudinal sectional view of the assembly 10 taken along line 13N-13N in the plan view of FIG. 13M. FIG. 13O is a perspective view of the assembly 10 shown in FIG. 13M. FIG. 13P is an enlarged detailed view of the portion of FIG. 13N within circle 13P. When in a finally locked configuration, the external surface of the head 24 contacts first step feature 40, second step feature 50 and third step feature 60, as shown in FIG. 13R, a detailed partial view of the portion of FIG. 13P within ellipse 13R.

The step features of the present invention are designed to increase strength and stability of the locking forces applied between tulip 14 and head 24. Polyaxial grip of the tulip 14 on the head 24 is enhanced. To establish a locked configuration, a compression force is established between head 24 and tulip 14. This is typically accomplished by applying force in a distal direction to the proximal end of head 24 while holding tulip 14 relatively stationary, applying force to tulip 14 in a proximal direction while holding head 24 relatively stationary, or most typically, applying force to head 24 in a distal direction while drawing tulip 14 in a proximal direction. Upon application of sufficient force (typically in the range of about 4.0 Nm to about 7.0 Nm, more typically in the range of about 5.0 Nm to 6.0 Nm, although the preferred force may vary depending upon the dimensions of the components, the materials from which they are made and whether provisional locking or final locking is intended, for example) the external surface of the head 24 and step features 40, 50, 60 (or only 40 and 50, for provisional locking) engage one another such that at least one of a portion of the external surface of the head 24 contacting the step feature 40 and step feature 40 partially deforms and typically a slight cold welding results. Likewise, at least one of a portion of the external surface of the head 24 contacting the step feature 50 and step feature 50 partially deforms and typically a slight cold welding results, resulting in provisional locking of the assembly (i.e., provisional locking of head 24 and fastener 12 relative to tulip 14). Upon application of more force, typically in the range of about 7.5 NM to about 12.5 Nm, more typically in the range of about 9.5 Nm to 10.5 Nm, at least one of a portion of the external surface of the head 24 contacting step feature 60 and step feature 60 also partially deforms and establishes additional (further augmented) cold welding, resulting in final locking of the head 24/fastener 12 relative to tulip 14, thereby providing enhanced polyaxial grip of the head by the tulip, as compared to the amount of polyaxial grip provided during provisional locking. This prevents movements of head 24 relative to tulip 14 even after completion of an implantation and vertebral derotation procedure and enables the locking configuration that the assembly is placed in to be maintained after completion of the procedure.

It is possible, if necessary to unlock the assembly 10 after a provisional or final locking condition has been established. This can be accomplished by removal of the compression force, after which a tool can be inserted into bore 32 to pry tulip 14 free from head 24, thereby breaking the cold welds, or by any other technique that breaks the cold welds, such as by proximal movement of head 24 relative to tulip 14 or distal movement of tulip 14 relative to head 24.

Preferably step features 40, 50 and 60 extend continuously about the entire inner circumference of bore 32, like that described above with regard to two-step feature embodiments. However, any or all of step features 40, 50 and 60 may be discontinuously provided in various arrangements. Any number of discontinuous first step features 40, any number of discontinuous second step features 50 and any number of discontinuous third step features 60 may be provided, with any circumferential positioning (relative to the circumference of bore 32) desired. Also, the step features 40, 50 and 60 may be aligned longitudinally with one another and/or staggered.

Referring now back to FIGS. 13F, 13L and 13R, a preferred configuration of the first, second and third step features 40,50,60 is described. A proximal end portion 40P that extends from the bore 32 is the portion of the step feature 40 that contacts the external surface of the head 24 and deforms and/or is partially deformed by head 24 during locking. Likewise, proximal end portion 50P that extends from the bore 32 is the portion of the step feature 50 that contacts the external surface of the head 24 during locking and partially deforms and/or is partially deformed by head 24 during locking, and proximal portion 60P that extends from the bore 32 is the portion of the step feature 60 that contacts the external surface of the head and partially deforms and/or is partially deformed by head 24 during final locking. A longitudinal surface 40L of first step feature 40 extends distally away from proximal end portion 40P and preferably extends tangentially and distally away from the external surface of head 24 when proximal portion 40P contacts the external surface of the head 24. Alternatively, the longitudinal surface 40L may extend away from the external surface of the head 24 at some other angle, but preferably does not contact the external surface of the head 24 even in the locked configuration. A longitudinal surface SOL of second step feature 50 extends distally away from proximal end portion 50P and preferably extends tangentially and distally away from the external surface of head 24 when proximal portion 50P contacts the external surface of the head 24. Alternatively, the longitudinal surface SOL may extend away from the external surface of the head 24 at some other angle, but preferably does not contact the external surface of the head 24 even in the locked configuration. A longitudinal surface 60L of third step feature 60 extends distally away from proximal end portion 60P and preferably away from the external surface of the head 24 at some angle relative to the longitudinal axis of the bore 32. In FIG. 13R surface 50L angles toward the center of bore 32 in a proximal to distal direction. Alternatively, surface 60L may extend tangentially and distally away from the external surface of head 24 when proximal portion 60P contacts the external surface of the head 24. In any case, surface 60L that is distal to portion 60P preferably does not contact the external surface of the head 24 even in the finally locked configuration, see FIG. 13R.

Referring to FIGS. 13B, 13H and 13N, the tulip 14 includes a slot extending therethrough normal to the longitudinal axis L-L of bore 32. Slot 14ST is configured and dimensioned to receive a rod, shaft, plate or channel for connection to assembly 10. A saddle 16 is configured and dimensioned to be fitted in the bore 32 of tulip 14 against the head 24 to prevent the head 24 from moving proximally relative to the tulip 14. Saddle 16 is configured and dimensioned to be fixed relative to tulip 14 while abutting the proximal portion of head 24. Saddle 16 has a concave distal surface 16S configured and dimensioned as a bearing surface to allow the convex curvature of head 24 to slide relative thereto. Accordingly, as shaft 22 is pivoted relative to tulip 14, head 24 rotates against bearing surfaces of the tulip 14/bore 32 and saddle 16. The limits of pivoting are established by the shaft 22 contacting against the tulip 14. Threading 14X in tulip 14 allows a set screw 46 (see FIG. 10) or other driving member to be torqued or otherwise driven against the rod, shaft, plate or channel to fix it relative to the tulip 14, and also to apply force to the saddle 16, which in turn drives compression of the head 24 relative to the step features 40, 50, 60 to establish a finally locked configuration, or against step features 40, 50 to establish a provisionally locked configuration. Thus, the saddle 16 is configured to apply compression to the head 24 to lock an orientation of the fastener 12 relative to the tulip 14, by driving the external surface of the head 24 against the first and second step features 40, 50 (as well as step feature 60 in the finally locked configuration).

All components 12,14, 16, 40, 50 and 60 of assembly 10 are preferably made of titanium. One or more components may be made of an alternative material such as cobalt chromium alloys, stainless steel, or any of the other alternative materials described above. The step features 40, 50 and 60 are preferably integrally made with the tulip 14, such as by machining, metal sintering, direct metal deposition or casting. Alternatively, the step features 40, 50, 60 can be integrally attached to the tulip to extend from the bore 32 in the manners described, by welding, or some other permanent attachment method that will not release even when the proximal portions of the step features 40, 50, 60 are plastically deformed under the compression forces. The dimensions of the components will vary depending upon the location of the spine (or elsewhere in the body) in which they are used, the size of the patient (e.g., pediatric vs. adult, male vs. female, etc.), etc. The outside diameter of tulip 14 typically falls within a range of about 8 mm to about 16 mm. The outside diameter of shaft 22 typically falls within a range of about 3 mm to about 10 mm. The length 22L of shaft 22 typically falls within a range of about 8 mm to about 100 mm. The inside diameter 38 of bore 32 is typically within the range of about 3 mm to about 11.5 mm. In the embodiment shown in FIGS. 13D, 13J and 13P, the inside diameter 38 is about 8.1 mm. In the embodiment shown in FIG. 12G, the inside diameter is about 9.6 mm. The outside diameter of head 24 is typically within the range of about 2.5 mm to about 11.5 mm. In the embodiment shown in FIGS. 13D, 13J and 13P, the outside diameter of head 24 is about 7.5 mm. Dimension 52 is typically in the range of about 2 mm to about 11 mm, more typically in the range of about 6 mm to about 9 mm. In one preferred embodiment, dimension 52 was about 7.05 mm. In another preferred embodiment, dimension 52 was about 8.55 mm. Dimension 42 is typically in the range of about 2.3 mm to about 11.3 mm, more typically in the range of about 6.3 mm to about 9.3 mm. Dimension 62 is typically in the range of about 1.7 mm to about 10.7 mm, more typically in the range of about 5.7 mm to about 8.7 mm. However, the dimensions 42, 52 and 62 may vary from these ranges, as dimensions of 38 and the outside diameter of head 24 vary. In one preferred embodiment, where dimension 52 was about 7.05 mm, dimension 42 was about 7.35 mm and dimension 62 was about 6.75 mm. In another preferred embodiment, where dimension 52 was about 8.55 mm, dimension 42 was about 8.85 mm and dimension 62 was about 8.25 mm. The tolerance between head 24 and bore 32 is typically in the range of about 0.3 mm to about 0.9 mm. In the embodiments of FIGS. 13D, 13J and 13P, the tolerance is about 0.6 mm±0.05 mm.

The present invention described with regard to the embodiments of FIGS. 13A-13Q provides capabilities that are not present in currently available polyaxial and uniplanar fastener assemblies. Not only can the fasteners 10 described in these embodiments be connected to a rod, the rod, shaft, plate or channel while allowing compression or distraction between vertebrae during a procedure, but they can also be provisionally locked with sufficient polyaxial grip in a provisional locking configuration, to allow tulip 14 to be levered with sufficient force to perform a derotation manipulation of a vertebra that the fastener is attached to, without disrupting the locked orientation of the tulip 14 relative to the head 24, but allowing the tulip 14 to rotate relative to the rod, that it is connected to. This is described in further detail below.

Figure 14B:
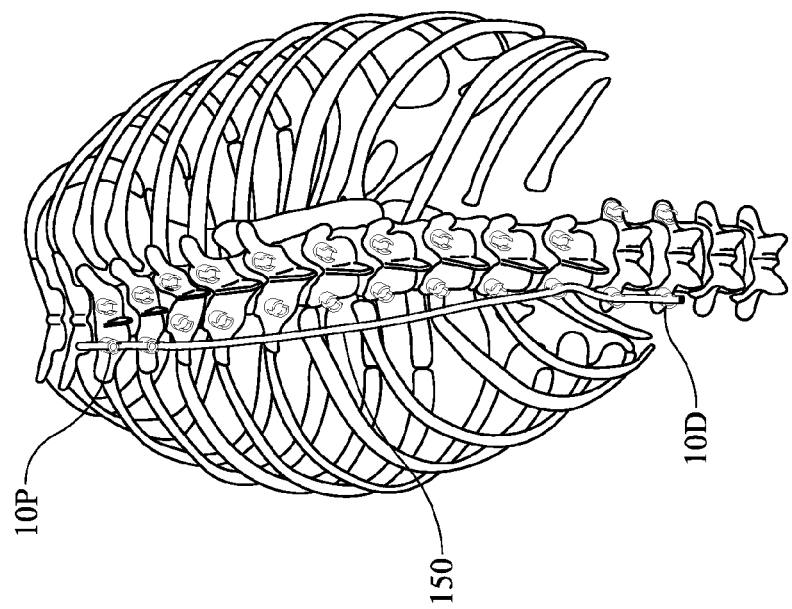
Figure 14A:
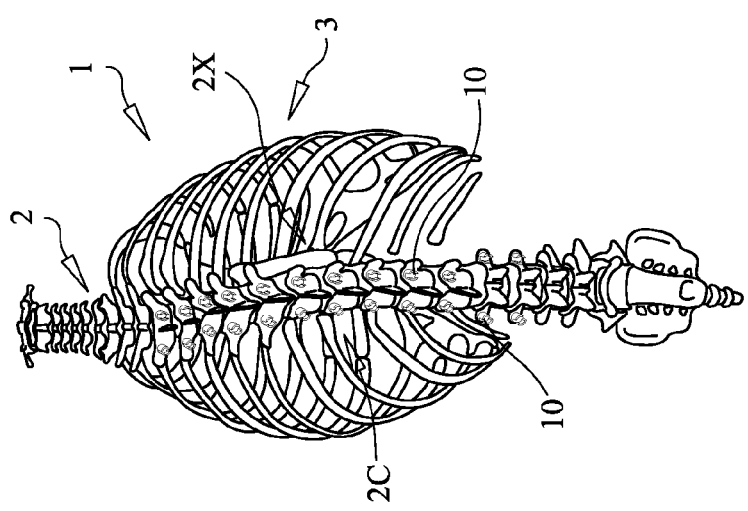
Figure 14D:
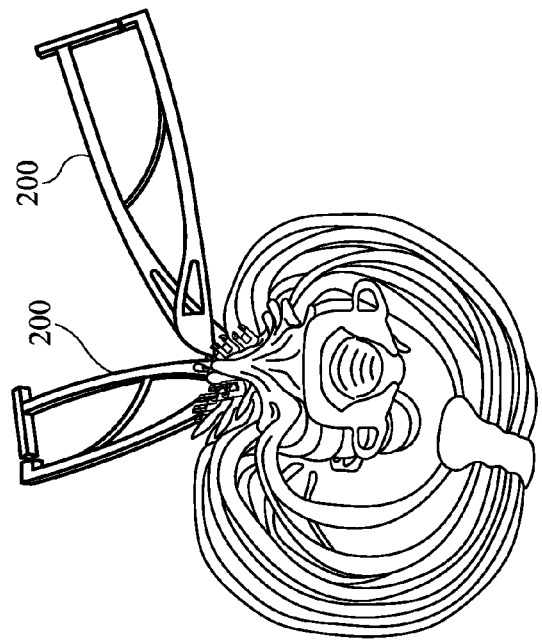
Figure 14C:
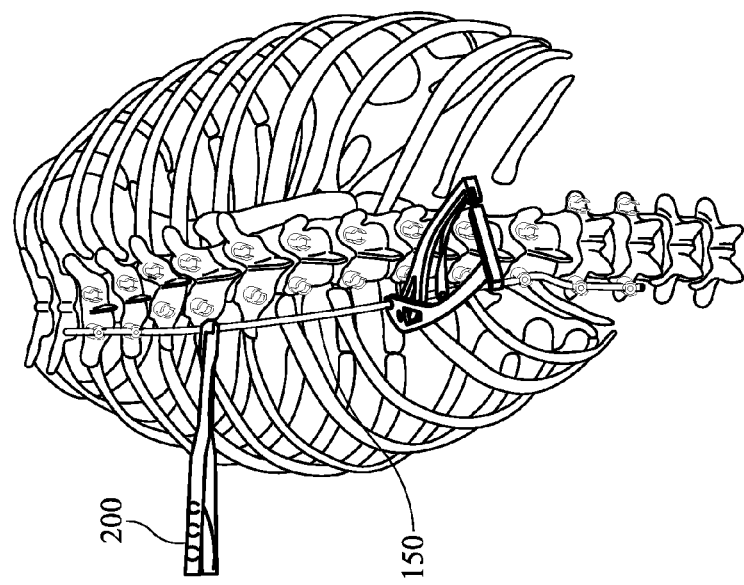
Figure 14E:
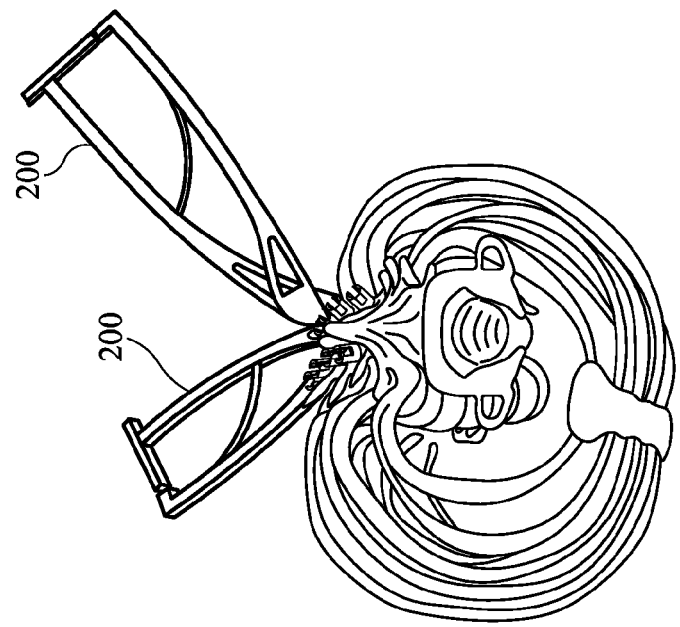
Figure 14F:
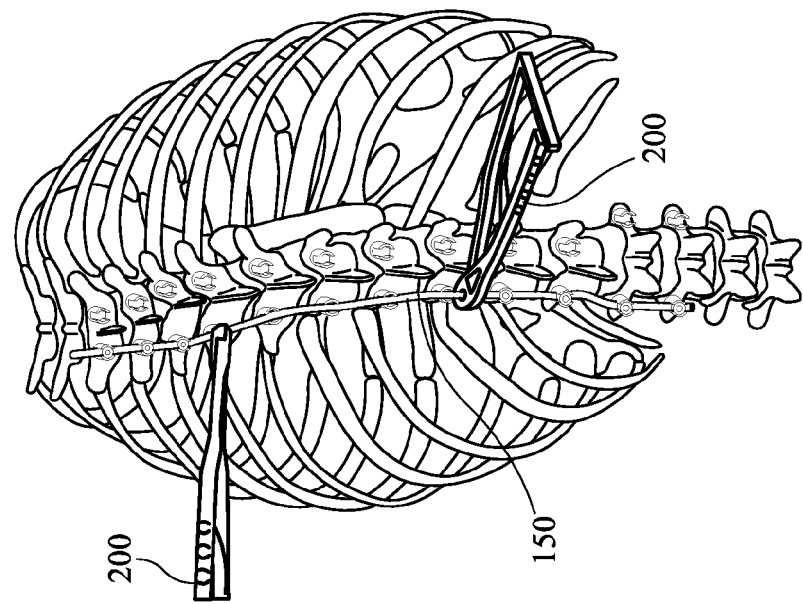
Figure 14H:
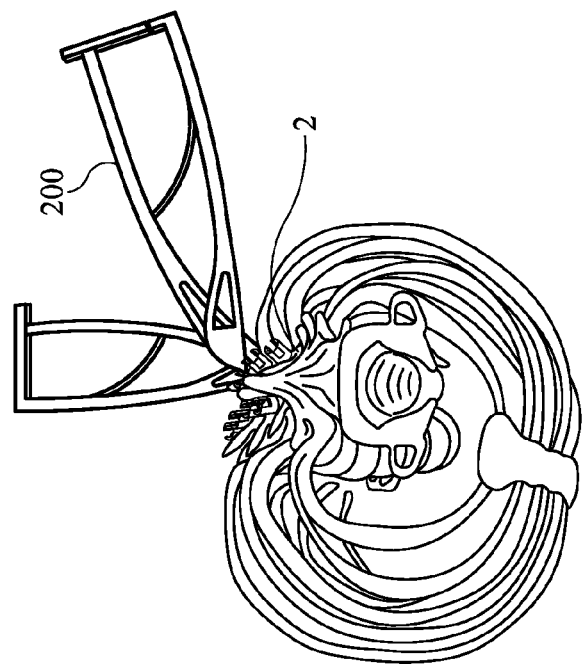
Figure 14G:
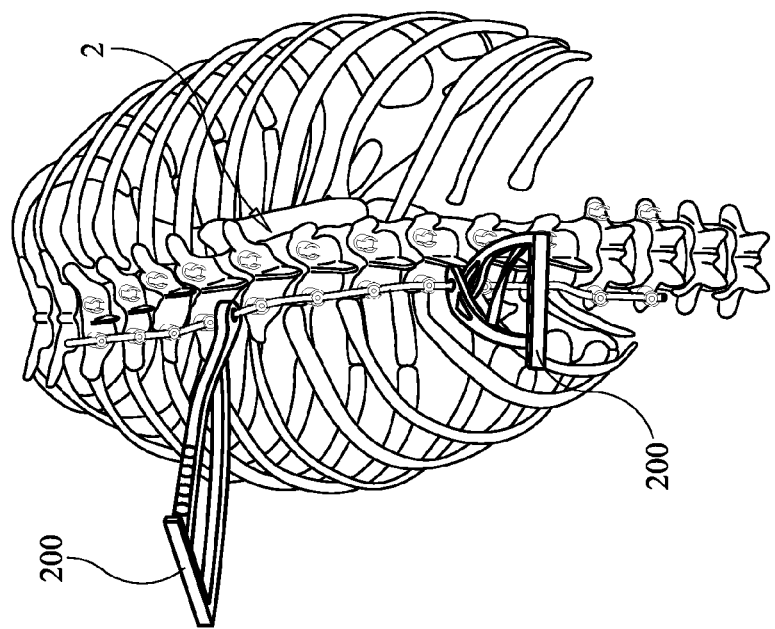
Figure 14J:
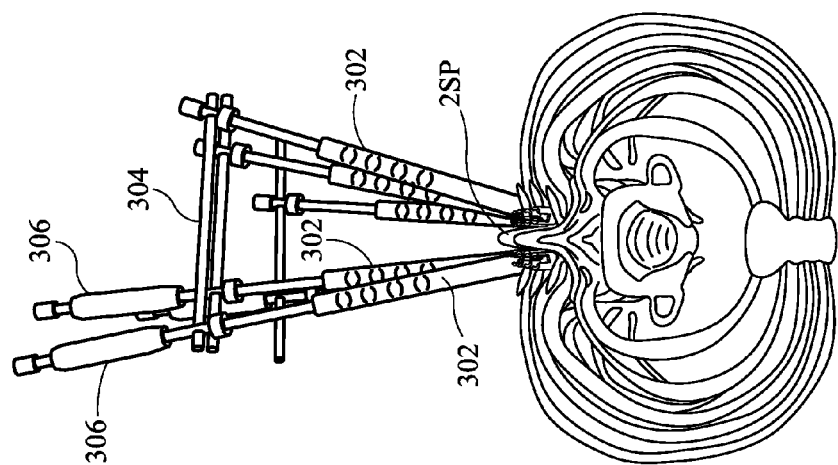
Figure 14I:
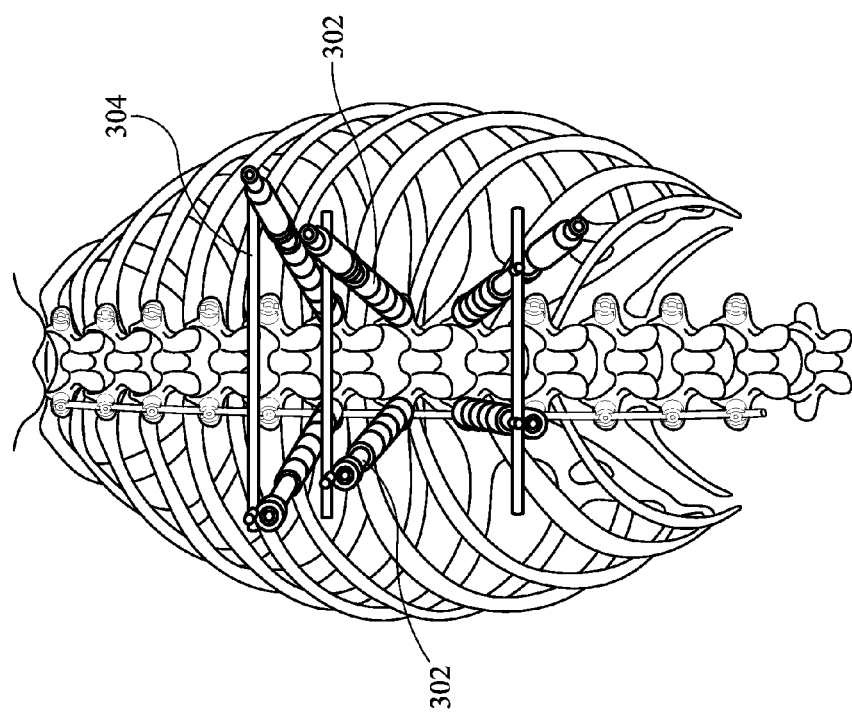
Figure 14N:
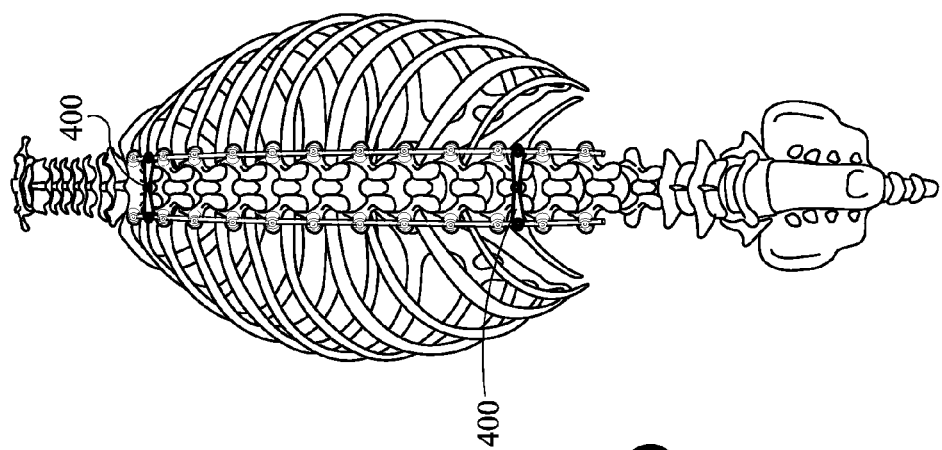

FIGS. 14A-14N illustrate steps that may be performed in carrying out a surgical procedure to correct spinal deformities such as scoliosis. The present invention is not limited to treatment of scoliosis, but is useful in surgical procedure used to treat other spinal deformities, diseases, etc. and can also be used for hard tissues of the body other than the vertebrae.

FIG. 14A illustrates the spinal column 2 and rib cage 3 of a patient suffering from Adolescent Idiopathic Scoliosis (AIS) exhibiting a Lenke 1 Curve. Using fasteners 10 of the embodiment of FIGS. 13A-13R, significant coronal plane correction can be consistently obtained. True axial plane correction can be achieved to address the rotational deformity of the spine 2, ribs 3 and chest wall of the patient 1. One of the deformities of the spine 2 in FIG. 1 that can be observed in FIG. 14A is that the spine 2 has a curvature such it presents a concave curvature 2C on the left side 50 and a convex curvature 2X on the right side.

After installation of fastener assemblies 10 into the vertebrae of the spine (see FIG. 14A), a rod 150 is implanted on the concave 2C side, see FIG. 14B. It is noted that all vertebrae that will need to be derotated have fasteners 10 of the type described with regard to the embodiment of FIGS. 13A-13R and/or monoaxial fasteners, (preferably with extended reduction tabs 14T, e.g., see FIGS. 15A-15C, if planning to perform a rod translation technique, in the concave 2C side, although in some cases tabs 14T will not be necessary) but that other types of monoaxial, uniplanar or polyaxial fasteners could be used in locations where derotation is not necessary, if such locations exist. Rod 150 is inserted into the slots 14S of the distal most and proximal most fasteners 10 and the set screw 46 of the proximal most fastener 10P tightened to lock the rod. This locking is a provisional locking if performing the classical Cotrel & Debussy "CD" rod rotation technique described in the following two paragraphs, but is a final locking if performing a rod translation technique. The set screw 46 of the distal most fastener 10D is tightened with a provisional locking force and then partially untightened, thereby provisionally locking fastener 2D, while leaving the rod 150 in the correct sagittal plane.

Rod clamps 200 (available from SpineCraft, LLC, Westchester, Ill.) are used to rotate the rod 150 into the tulips 14 (slots 14ST) of the apical fasteners (fasteners 10 attached to the pedicles of the vertebrae intermittent of the proximal most and distal most fasteners), see the posterior view (FIG. 14C) and distal view (FIG. 14D). Once the rod 150 has been inserted into a slot 14ST, set screw 46 is installed so as to maintain the capture of the rod 150 in the tulip. The set screws 46 of the apical fasteners 10 are installed—torqued with a force sufficient to provisionally lock the apical fasteners in a manner described above, and then partially untightened to allow free rotation of the tulips 14 around the rod 150 during vertebral body derotation maneuvers described below.

At FIGS. 14G-14H, the rod clamps are used to counter-rotate the rod 150 by an amount equal and opposite to the amount that it was rotated in FIGS. 14E-14F so as to return the rod 150 to its position in 14B, while at the same time bringing the spine 2 into sagittal alignment. By comparing FIGS. 14G and 14A, it can be observed that the spine 2 is now relatively straight in the sagittal plane, with the convex 2X and concave 2C curvatures having been substantially removed. Even through the spine 2 is now substantially correctly aligned in the sagittal plane, it is often the case that one or more vertebrae can still be rotated relative to its normal position, such that the spinous process 2SP is not vertical (12 O'clock position) when viewed in the transverse plane (like the view in FIG. 14J). In order to correct this type of deformity, a rotation of the abnormally oriented vertebra/vertebrae is/are needed.

Figure 13M:
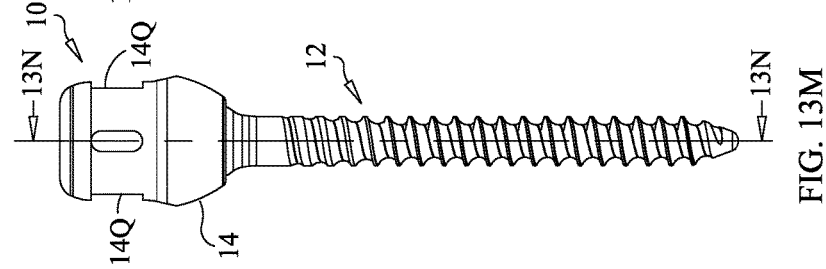
Figure 15D:
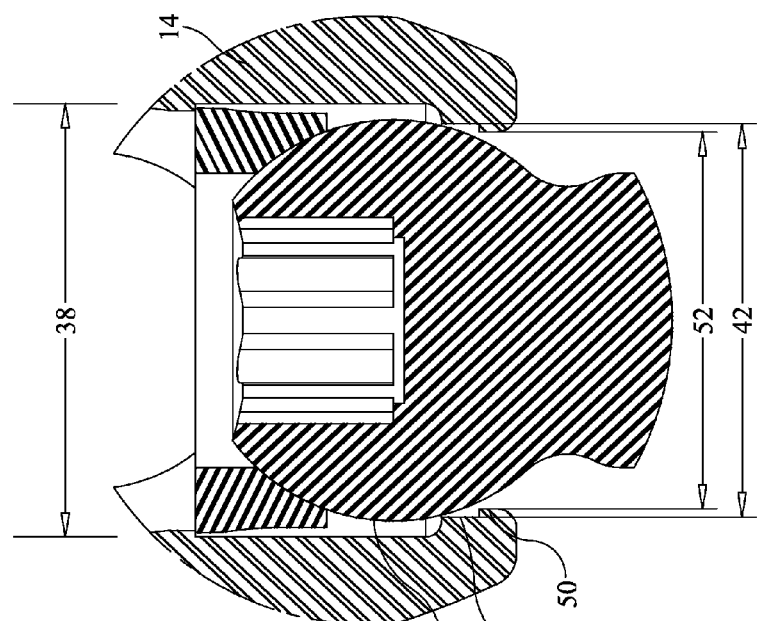
Figure 15C:
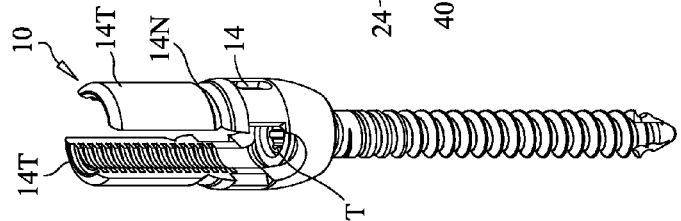
Figure 15E:
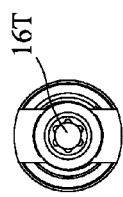
Figure 15B:
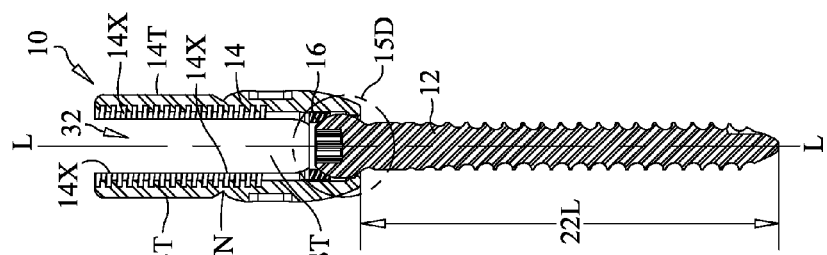
Figure 15A:
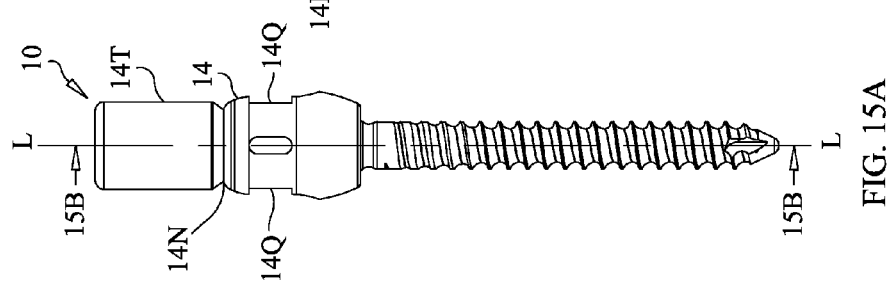

In FIGS. 14I-14J, derotator posts 302 (available from SpineCraft, LLC, Westchester, Ill.) are attached to the tulips 14 (for example, by having the prongs on the sides of the derotator posts 302 to interface with and lock to the QUAD RECESSES 14Q in the tulips 14, e.g. see FIGS. 13M and 15A, of the apical fasteners 10, and opposing posts 302 that are attached to the same vertebra are connected by a transverse link 304 (available from SpineCraft, LLC, Westchester, Ill.). A handle 306 is attached to one or more of the derotator posts 302 of each derotator 300 (pair of posts connected by transverse link) to provide additional leverage for applying torque. Derotational torque (leverage) is then applied to each vertebra needing to be rotated by application of force to handles 306 This derotational torque (leverage) can be applied sequentially or simultaneously to all vertebrae needing to be derotated, but typically, the preferred approach is to use a combination of both, i.e., sequential rotation is applied to partially derotate, followed by en bloc derotation for final correction, to arrange the vertebrae properly such that the spinous processes 2SP are substantially vertically aligned as in FIG. 14J. The spine 2 is thus derotated, reducing rib prominence on the convex side and restoring coronal alignment of the spine 2.

Fasteners 10 attached to the vertebrae to be rotated are placed in the provisional locking configuration prior to vertebral body derotation. This is accomplished by torquing the set screws 46 to apply a provisional locking force that is typically about half of the amount of force used to finally lock the fasteners. Once axial alignment has been achieved through derotation as described, the set screws 46 are further torqued to apply the full force needed to place the fasteners 10 on the concave side in the final locking configuration, see FIG. 14K. There is typically no need for compression and/or distraction at the levels of the apical vertebrae, but if this is required, alternate level/side sequential loosening to the provisionally locked fasteners 10 and then final locking is performed respectively before and after the segmental compression/distraction, see FIG. 14K. Fastener 10 of FIGS. 13A-13R, when in the provisional locking configuration, maintains the fastener 10 in a locked state, even after the force applied by the set screw 46 has been removed, due to the deformation of the components in contact (head 24 and step features 40, 50) and resulting cold welding. For this reason, the set screws 46 can be loosened after placing the fasteners 10 into the provisional locking configuration, but still maintained by the threads 14X of the tulip 14. This maintains capture of the rod 150, while at the same time allowing relative rotation between the tulips 14 and the rod 150 during derotation, and while maintaining the orientational relationship between each tulip 14 and its respective head 24. In the provisional locking configuration, the tulip 14 can withstand a levering force of about 100 to about 200 Newtons, typically about 150 Newtons, without breaking loose of the head 24 and thus still maintaining polyaxial grip, such that the fastener 10 moves as a unit and the tulip 14 does not rotate relative to the head 24. Once the derotation is completed, the set screws 46 on the concave side are tightened to the final locking configuration to maintain the rotational positions of the tulips 14 relative to the shaft 150. In the final locking configuration, the tulip 14 can withstand a levering force of about 350 to about 550 Newtons, typically about 450 Newtons, without breaking loose of the head 24 and thus still maintaining polyaxial grip, such that the fastener 10 remains fixed in its orientation and the tulip 14 does not rotate relative to the head 24 or the rod 150.

After tightening the set screws 46 on the concave side, the derotator assemblies 300 are removed and a second rod 150 is implanted on the convex side, see FIG. 14L, the fasteners 10 on the convex side then being placed in the provisional locking configuration by application of force through torquing the respective set screws 46.

Figure 14M:
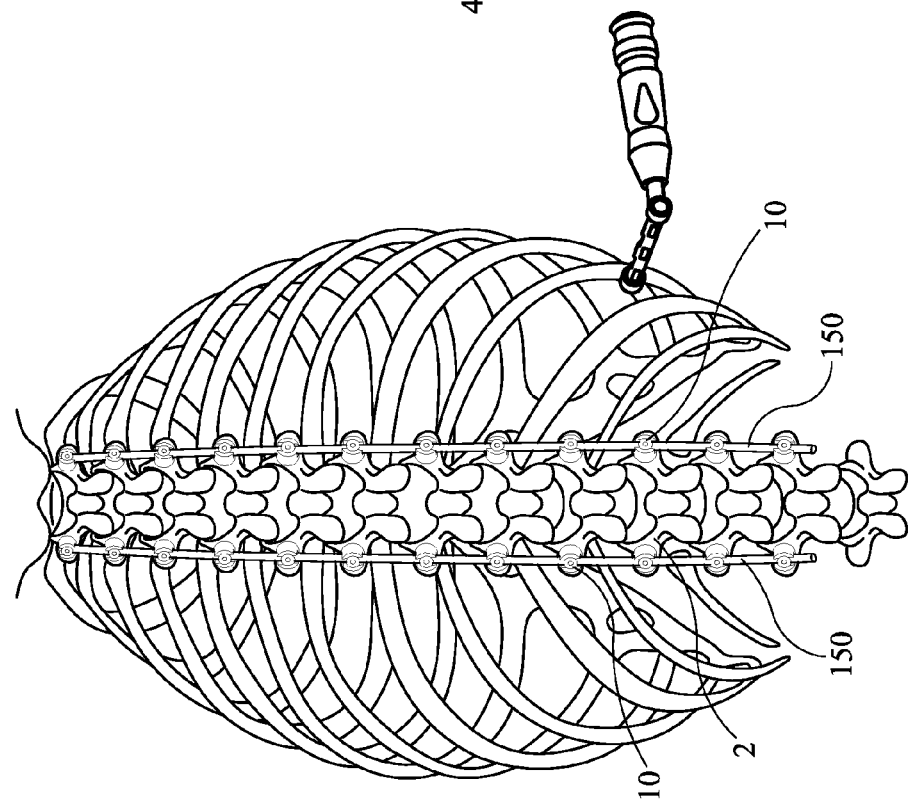

Next, the spine 2 is compressed or distracted as needed (FIG. 14M) according to known techniques, after which the set screws are re-torqued with sufficient force to place all fasteners into the final locking configuration. Cross connectors 400 (available from SpineCraft, LLC, Westchester, Ill.) are then attached to the rods 150 at or near their extremities, see FIG. 14N, and the procedure is completed according to known practices.

FIGS. 15A-15E illustrate a fastener 10 with extended reduction tabs 14T according to an embodiment of the present invention. FIGS. 15A-15E depict a fastener 10 of the type shown in FIGS. 12A-12E, except that the tulip 14 and channel 32 have been extended by reduction tabs 14T that extend proximally from the proximal end of tulip 14 as it is shown in FIG. 12A. It is noted that extended reduction tabs 14T are not limited to modification of the embodiment of FIGS. 12A-12E, but can be likewise provided on any of the embodiments described herein, as well as on any tulip of any monoaxial, uniplanar, multi-planar or polyaxial fastener.

FIG. 15A is a plan view of the surgical screw assembly 10 with reduction tabs 14T. In the embodiment of FIG. 15A, the surgical screw assembly is a polyaxial surgical screw assembly, meaning that, in an unlocked condition, shaft 22 can pivot relative to tulip 14 in any plane. However, the locking force augmentation features (e.g., the step features, arrangement and functioning of the tulip and head, and methods of providing enhanced locking force) as described with this embodiment are equally applicable to uniplanar surgical screw assemblies, such as those described above, as well as screw assemblies that can pivot in multiple planes but not all planes, and generally to all polyaxial and uniplanar screw assemblies to provide enhanced locking force.

Reduction tabs 14T are integrally provided to extend from the main body of tulip 14. Alternatively, reduction tabs 14T can be joined to tulip 14 by welding or other equivalent attachment means, provided that the reduction tabs 14T can be readily separated from the main body tulip 14, such as by breaking them off. In the embodiment shown in FIG. 15A, reduction tabs 14T are formed integrally with tulip 14 by machining, metal sintering, direct metal deposition or casting or the like. A weakened section such as neck region 14N is provided at the junction of each reduction tab 14T with the main body of the tulip 14, to facilitate readily breaking off the reduction tabs 14T from tulip 14 thereby separating them. A reduction fastener 10 is used in situations such as when a vertebra has been pushed forward (anteriorly slipped) such that it resides at a lower level than the rest of the vertebrae when the patient is lying on his/her stomach. In these situations, a fastener 10 without reduction tabs 14T, when installed into such a vertebra, becomes oriented such that the rod 150 cannot reach the slot 14ST to be received therein so that the driver 46 can be installed into the slot 14ST and driven against the rod 150 to draw up the vertebra. To remedy this, extended reduction tab fastener 10 includes reduction tabs 14T that extend the slot 14EST so that the slot reaches the rod 150, and allows rod 150 to be received therein sufficiently to install driver 46 on top of rod 150 to be driven against the rod 150 and draw up the vertebra.

FIG. 15B is a longitudinal sectional view of the assembly 10 taken along line 15B-15B in FIG. 15A. FIG. 15C is a perspective view of the assembly 10 of FIG. 15A. FIGS. 15B-C illustrate that there are two reduction tabs 14T, one on each side of slot 14EST. Of course, some other number of reduction tabs 14T could be provided, so long as they adequately function to extend the slot 14EST, to draw up the vertebra as described, and are readily removable. In the embodiment shown in FIG. 15B, reduction tabs 14T extend the slot 14ST to form extended slot 14EST which is more than twice as long as slot 14ST of FIG. 12A or the slot formed solely by the main body of the tulip 14 in FIG. 15B. Reduction tabs 14T typically have a length selected from the range of about 10 mm to about 200 mm, more typically from the range of about 15 mm to about 125 mm. Reduction tabs 14T are provided with threading 14X that cooperates continuously with the threading 14X in the slot 14ST of the main body of the tulip 14. In this way, driver 46 can be seamlessly threaded through the reduction tabs 14T and into the main body of the tulip 14, as the vertebra is drawn up and the main body of the tulip 14 is drawn over the rod 150 such that rod 150 is received in the slot 14ST of the main body of the tulip 14. Once this has been accomplished, the reduction tabs 14T can be broken off from the tulip and removed from the surgical site.

The assembly 10 of the embodiment of FIGS. 15A-15E includes a fastener 12 including an elongate shaft 22 and a head 24 at a proximal end of the shaft 22. As shown, elongate shaft 22 is a screw shaft having threads 26 therealong. Head 24 is substantially spherical, having a convex external surface. A tulip 14 has a bore 32 therethrough that defines a bearing surface against which head 24 can rotate when assembly 10 is in an unlocked configuration. Bore 32 is dimensioned to allow the distal end of elongate shaft 12 to pass therethrough as well as to allow the head 24 to be inserted into the tulip 14.

FIG. 15D is an enlarged detailed view of the portion of FIG. 15B within circle 15D. A first step feature 40 is located at a distal end portion of bore 32 and extends inwardly therefrom. The first step feature 40 reduces the diameter 38 of bore 32 to a dimension 42 that allows the distal end of the elongate shaft to pass therethrough, and allows all of the shaft 22 to pass therethrough, but prevents passage of head 24 therethrough as a portion of the first step feature contacts the external surface of the head, as shown in FIG. 15D. A second step feature 50 is located at a distal end portion of bore 32, distally of first step feature 40. Second step feature 50 further reduces the diameter of bore 32 to a dimension 52 less than dimension 42 established by first step feature 40, the further reduced dimension 52 allowing the distal end of the elongate shaft 22 to pass therethrough, and allows all of the shaft 22 to pass therethrough, but prevents passage of head 24 therethrough.

FIG. 15E is a top view of the assembly 10 of FIG. 15A. A tool interface 16T is provided in the proximal end of head 24 that can be interfaced by a tool to drive the fastener 12 into the bone. The present invention is not limited to this type of interface as any other equivalent type of torquing interface could be used.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

That which is claimed is:

1. A surgical screw assembly comprising:
    a fastener including an elongate shaft having a proximal end and a distal end and a head at said proximal end, said head having an external surface;
    a tulip having a tulip proximal end portion, a tulip distal end portion, an external surface and an internal bearing surface, said tulip distal portion end having a bore therethrough defining said internal bearing surface and having a diameter dimensioned to allow said distal end of said elongate shaft to pass therethrough, and a channel transverse to said bore configured to receive a support member;
    wherein, in an unlocked configuration, said head is movable relative to said tulip and said support member is movable relative to said tulip; in a provisionally locked configuration, said head is fixed relative to said tulip and said support member is movable relative to said tulip; and in a finally locked configuration, said head is fixed relative to said tulip and said support member is fixed relative to said tulip.

2. The assembly of claim 1, wherein in said provisionally locked configuration, said head engages said tulip with a first grip strength; and in said finally locked configuration, said head engages said tulip with a second grip strength, said second grip strength being greater than said first grip strength.

3. The assembly of claim 1, further comprising a threaded driver configured to be threaded into said tulip, wherein said threaded driver is driven against said support member to establish said provisionally locked configuration, and is further driven against said support member to establish said finally locked configuration.

4. The assembly of claim 3, wherein said threaded driver can be reverse threaded away from said support member, in said provisionally locked configuration, to reduce compression against said support member while said head remains provisionally locked to said tulip.

5. The assembly of claim 1, wherein, when implanted in a vertebra of a spine of a patient, when in said provisionally locked configuration, and when a provisional locking compression force has been removed, said provisionally locked configuration has sufficient locking strength to prevent relative movement between said tulip and said head when said tulip is driven to cause rotation of the vertebra.

6. The assembly of claim 1, further comprising reduction tabs extending proximally of said tulip and extending said channel.

7. The assembly of claim 1, further comprising a saddle, said saddle being configured and dimensioned to be fitted in said tulip proximally of and against said head.

8. The assembly of claim 7, further comprising at least one protrusion extending from said saddle and at least one slot formed in a surface of said head and configured to receive said at least one protrusion, respectively;
wherein said at least one protrusion and said at least one slot respectively interface to allow said head to angulate relative to said tulip in a predetermined plane, but prevent said head from angulating in other planes relative to said tulip.

9. The assembly of claim 7, further comprising at least one flat formed on a surface of said saddle and at least one flat formed on said head;
wherein said at least one flat on said saddle and said at least one flat of said head respectively interface to allow said head to angulate relative to said tulip in a predetermined plane, but prevent said head from angulating in other planes relative to said tulip.

10. The assembly of claim 1, further comprising at least one protrusion extending inwardly from an inward surface of said tulip; and at least one slot formed in said head and configured to receive said at least one protrusion, respectively;
wherein said at least one protrusion and said at least one slot allow said head to angulate relative to said tulip in a predetermined plane, but prevent said head from angulating in other planes relative to said tulip.

11. The assembly of claim 10, wherein each said at least one protrusion comprises an insert fixed to said tulip.

12. The assembly of claim 10, wherein said at least one protrusion is formed integrally with said tulip.

13. The assembly of claim 1, further comprising at least one flat formed on a surface of said head and at least one flat formed in a surface of said tulip;
wherein said at least one flat of said head and said at least one flat of said tulip respectively interface to allow said head to angulate relative to said tulip in a predetermined plane, but prevent said head from angulating in other planes relative to said tulip.

14. The assembly of claim 13, wherein said at least one flat of said tulip comprises an insert.

15. The assembly of claim 1, further comprising at least one protrusion extending from a surface of said head and at least one slot formed in an inner surface of said tulip and configured to receive each said at least one protrusion respectively;
wherein said at least one protrusion and said at least one slot respectively interface to allow said head to angulate relative to said tulip in a predetermined plane, but prevent said head from angulating in other planes relative to said tulip.

16. The assembly of claim 15, wherein said at least one protrusion comprises an insert.

17. The assembly of claim 15, wherein said at least one protrusion is formed integrally with said head.

18. A method of operating a surgical screw assembly, said method comprising:
providing a surgical screw assembly comprising: a fastener including an elongate shaft having a proximal end and a distal end and a head at said proximal end, said head having an external surface; a tulip having a tulip proximal end portion, a tulip distal end portion, an external surface and an internal bearing surface, said tulip distal end portion having a bore therethrough defining said internal bearing surface and having a diameter dimensioned to allow said distal end of said elongate shaft to pass therethrough;
attaching a support member to said assembly;
applying a first compression force through said support member to provisionally lock said head to said tulip in a provisionally locked configuration;
wherein, in said provisionally locked configuration, said tulip is prevented from rotating relative to said head, but said tulip is movable relative to the support member.

19. The method of claim 18, wherein said fastener further comprises reduction tabs extending proximally form said tulip, and wherein said attaching a support member comprises positioning the support member between the reduction tabs, relatively moving the fastener and the support member toward one another so that the support member is positioned within the tulip, and removing the reduction tabs from the tulip after said attaching a support member to said assembly.

20. The method of claim 18, further comprising relatively rotating one of the support member and said tulip relative to the other, while said provisionally locked configuration prevents said tulip from rotating relative to said head.

21. The method of claim 18, further comprising removing the first compression force, whereby said head is maintained provisionally locked to said tulip after said removing the first compression force.

22. The method of claim 18, further comprising:
applying a second compression force greater than said first compression force through the support member to finally lock the assembly in a finally locked configuration;
wherein, in said finally locked configuration, said tulip is prevented from rotating relative to said head, and said tulip is prevented from moving relative to the support member.

* * * * *